United States Patent
Hong et al.

(10) Patent No.: US 10,523,258 B2
(45) Date of Patent: Dec. 31, 2019

(54) COMMUNICATION DEVICE TO PERFORM WIRELESS COMMUNICATION AND WIRELESS POWER TRANSFER, AND ELECTRODE DEVICE TO TRANSMIT AND RECEIVE ELECTRICAL SIGNAL FROM TARGET

(71) Applicant: Samsung Electronics Co., Ltd., Suwon-si (KR)

(72) Inventors: Young Jun Hong, Seoul (KR); Jaechun Lee, Seoul (KR); Joonseong Kang, Suwon-si (KR); Wonseok Lee, Yongin-si (KR); Junyeub Suh, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 15/898,316

(22) Filed: Feb. 16, 2018

(65) Prior Publication Data
US 2018/0254793 A1    Sep. 6, 2018

(30) Foreign Application Priority Data

Mar. 6, 2017   (KR) .......... 10-2017-0028377
Nov. 13, 2017  (KR) .......... 10-2017-0150580

(51) Int. Cl.
*H04B 1/40*    (2015.01)
*H02J 50/12*   (2016.01)
(Continued)

(52) U.S. Cl.
CPC .......... *H04B 1/40* (2013.01); *A61N 1/0551* (2013.01); *A61N 1/0556* (2013.01); *H02J 50/12* (2016.02);
(Continued)

(58) Field of Classification Search
CPC ...... H04B 1/40; H04B 5/0031; H04B 5/0037; H02J 50/12; H02J 7/025
See application file for complete search history.

(56) References Cited

U.S. PATENT DOCUMENTS 9,242,105 B2   1/2016  Brockway et al.
9,409,023 B2   8/2016  Burdick et al.
(Continued)

FOREIGN PATENT DOCUMENTS

JP   10203059      *  8/1998
JP   2004-21484 A     1/2004
(Continued)

OTHER PUBLICATIONS

Extended European Search Report dated Jun. 8, 2018, in corresponding European Application No. 181598921 (7 pages, in English).
(Continued)

*Primary Examiner* — Nguyen T Vo
(74) *Attorney, Agent, or Firm* — NSIP Law

(57) ABSTRACT

A communication device includes: a coil disposed around a core area of the communication device; a processor disposed in the core area and configured to establish communication with an external device through the coil; and a discrete element disposed on the coil and connected to the processor through a via.

18 Claims, 27 Drawing Sheets

(51) Int. Cl.
*A61N 1/05* (2006.01)
*H04B 5/00* (2006.01)
*H02J 7/02* (2016.01)

(52) U.S. Cl.
CPC ......... *H04B 5/0031* (2013.01); *H04B 5/0037* (2013.01); *H02J 7/025* (2013.01)

(56) References Cited

U.S. PATENT DOCUMENTS

| | | | |
|---|---|---|---|
| 2003/0103015 A1* | 6/2003 | Oh | H01Q 1/246 343/867 |
| 2004/0124983 A1* | 7/2004 | Kuroda | G06K 19/0723 340/572.1 |
| 2011/0054583 A1 | 3/2011 | Litt et al. | |
| 2011/0112601 A1 | 5/2011 | Meadows et al. | |
| 2011/0224767 A1 | 9/2011 | Inman | |
| 2013/0310911 A1 | 11/2013 | Tai et al. | |
| 2013/0328723 A1* | 12/2013 | Rappaport | H04B 1/3838 342/372 |
| 2015/0170017 A1 | 6/2015 | Murayama et al. | |
| 2016/0067497 A1 | 3/2016 | Levine et al. | |
| 2016/0121115 A1 | 5/2016 | Guillory et al. | |
| 2016/0126744 A1 | 5/2016 | Jeong et al. | |
| 2016/0196230 A1* | 7/2016 | Pihet | G06F 13/4027 710/314 |
| 2017/0047636 A1 | 2/2017 | Lee et al. | |
| 2017/0290157 A1 | 10/2017 | Sturcken et al. | |

FOREIGN PATENT DOCUMENTS

| | | |
|---|---|---|
| JP | 2008-146567 A | 6/2008 |
| JP | 2014-514043 A | 6/2014 |
| KR | 10-1183558 B1 | 9/2012 |
| KR | 10-2013-0045306 A | 5/2013 |
| KR | 10-2013-0112233 A | 10/2013 |
| KR | 10-2018-0055069 A | 5/2018 |
| WO | WO 2017/036895 A1 | 3/2017 |

OTHER PUBLICATIONS

Extended European Search Report dated Jul. 24, 2018, in corresponding European Application No. 181583048 (7 pages, in English).

Frieda Koopman, et al., "Pilot Study of Stimulation of the Cholinergic Anti-inflammatory Pathway with an Implantable Vagus Nerve Stimulation Device in Patients with Rheumatoid Arthritis," *Proceedings of the ACR/ARHP Annual Meeting,* Washington, DC, Nov. 2012 (1 page, in English).

* cited by examiner

COMMUNICATION DEVICE TO PERFORM WIRELESS COMMUNICATION AND WIRELESS POWER TRANSFER, AND ELECTRODE DEVICE TO TRANSMIT AND RECEIVE ELECTRICAL SIGNAL FROM TARGET

CROSS-REFERENCE TO RELATED APPLICATIONS

This application claims the benefit under 35 USC § 119(a) of Korean Patent Application No. 10-2017-0028377 filed on Mar. 6, 2017, and Korean Patent Application No. 10-2017-0150580 filed on Nov. 13, 2017, in the Korean Intellectual Property Office, the entire disclosures of which are incorporated herein by reference for all purposes.

BACKGROUND

1. Field

The following description relates to a communication device and an electrode device.

2. Description of Related Art

Amid the development of communication technology and wireless power transfer technology, such as, for example, short-range wireless communication and Bluetooth, an electronic device, for example, a mobile communication device includes an antenna device that operates in various different frequency bands.

By using multiple antenna modules, transmission and reception of a wireless signal of various frequency bands and a wireless power transmission and reception may be enabled, and also a data transfer rate and a wireless power transfer rate in the transmission and reception may be improved. However, due to a limited space for the antenna modules, a size of the antenna modules to be mounted in a mobile communication device may be restricted.

SUMMARY

This Summary is provided to introduce a selection of concepts in a simplified form that are further described below in the Detailed Description. This Summary is not intended to identify key features or essential features of the claimed subject matter, nor is this Summary intended to be used as an aid in determining the scope of the claimed subject matter.

In one general aspect, a communication device includes: a coil disposed around a core area of the communication device; a processor disposed in the core area and configured to establish communication with an external device through the coil; and a discrete element disposed on the coil and connected to the processor through a via.

The processor may be disposed in a layer distinguished from the coil.

The discrete element may include a passive element configured to separate voltages of circuits in a chip including the processor.

The discrete element may include any one or any combination of any two or more of a capacitor, an inductor, and a resistor, which is connected to a chip including the processor through the via, and is arranged in an outer edge ring area of the coil in a layer distinguished from the coil.

The communication device may further include: a first transceiver circuit configured to transmit and receive, through the coil, a signal of a first bandwidth; and a second transceiver circuit configured to transmit and receive, through the coil, a signal of a second bandwidth that is different from the first bandwidth, wherein the first transceiver circuit and the second transceiver circuit are included in a chip including the processor.

The first transceiver circuit may be configured to operate at a voltage less than or equal to a first threshold voltage. The second transceiver circuit may be configured to operate at a voltage greater than or equal to a second threshold voltage that is greater than the first threshold voltage.

The communication device may further include: an electrode router circuit connected to electrodes, wherein the electrode router circuit is included in a chip including the processor.

The electrode router circuit may be configured to connect a first electrode among the electrodes to a sensing circuit, and connect a second electrode among the electrodes to a driving circuit. The sensing circuit may be configured to detect, through the first electrode, an electrical signal corresponding to a point to which the first electrode is attached. The driving circuit may be configured to apply, through the second electrode, an electrical signal to a point to which the second electrode is attached.

The sensing circuit may be configured to operate at a voltage less than or equal to a first threshold voltage. The driving circuit may be configured to operate at a voltage greater than or equal to a second threshold voltage that is greater than the first threshold voltage.

The coil may include a first partial coil configured to resonate in a first bandwidth, and a second partial coil configured to resonate in a second bandwidth that is different from the first bandwidth. The first partial coil and the second partial coil may share a loop.

The first partial coil may include a loop configured to generate a magnetic field in a first direction. The second partial coil may include a loop configured to generate an electric field in the first direction.

The communication device may further include: an embedded element disposed in a layer distinguished from a layer including the coil and a layer including the processor, and connected to the processor through the via; and a motion sensor configured to sense a motion of the communication device.

A chip including the processor may be spaced from the coil by a distance greater than or equal to a threshold distance.

The processor may be connected to electrodes arranged to cover a target, and may be configured to receive an electrical signal from or provide an electrical signal to some of the electrodes.

The processor may be configured to allocate a sensing channel to one or more electrodes among the electrodes, and allocate a stimulating channel to one or more remaining electrodes among the electrodes, based on the received electrical signal.

In another general aspect, an electrode device includes: a substrate formed of a flexible material and configured to cover a target; electrodes disposed on a face of the substrate that is configured to be in contact with the target in a longitudinal direction of the substrate; and an electrode router configured to connect the electrodes to a processor.

The substrate may helically cover the target.

The electrode router may be configured to transfer, to the processor, an electrical signal detected through a first electrode among the electrodes, and apply an electrical signal to a point of the target that is in contact with a second electrode, among the electrodes, that is different from the first electrode.

The processor may be configured to allocate a sensing channel of the electrode router to one or more electrodes among the electrodes, and allocate a stimulating channel of the electrode router to one or more remaining electrodes among the electrodes.

The electrodes may be classified based on channels, and electrodes corresponding to a same channel among the channels may be disposed to be adjacent to each other on the substrate.

The electrodes may be classified based on channels, and electrodes corresponding to a same channel among the channels may be arranged not to be adjacent to each other on the substrate.

The processor may be configured to allocate a sensing channel of the electrode router to one or more electrodes among the electrodes, and allocate a stimulating channel of the electrode router to one or more other electrodes among the electrodes, based on an electrical signal detected from the target.

The processor may be configured to allocate channels to the electrodes and arrange electrodes corresponding to a same channel among the channels to be adjacent to each other on the substrate, in response to common noise of a value greater than or equal to a threshold value being included in an electrical signal detected from the target.

The processor may be configured to allocate channels to the electrodes and arrange electrodes corresponding to a same channel among the channels not to be adjacent to each other on the substrate, in response to common noise of a value less than a threshold value being included in an electrical signal detected from the target.

In another general aspect, a wireless device includes: a substrate configured to cover a nerve; electrodes disposed on the substrate and configured to contact the nerve; an electrode router connected to the electrodes; and a processor configured to allocate the electrodes to channels based on a common noise in a signal from the nerve.

The channels may include a stimulating channel to stimulate the nerve and a sensing channel to sense the signal from the nerve.

The processor may be further configured to allocate first adjacent electrodes among the electrodes to the stimulating channel, in response to a value of the common noise being greater than or equal to a threshold value, and allocate second adjacent electrodes among the electrodes to the sensing channel, in response to the value of the common noise being greater than or equal to the threshold value.

The processor may be further configured to allocate first non-adjacent electrodes among the electrodes to the stimulating channel, in response to a value of the common noise being less than a threshold value, and allocate second non-adjacent electrodes among the electrodes to the sensing channel, in response to the value of the common noise being less than the threshold value.

Other features and aspects will be apparent from the following detailed description, the drawings, and the claims.

Figure 1:
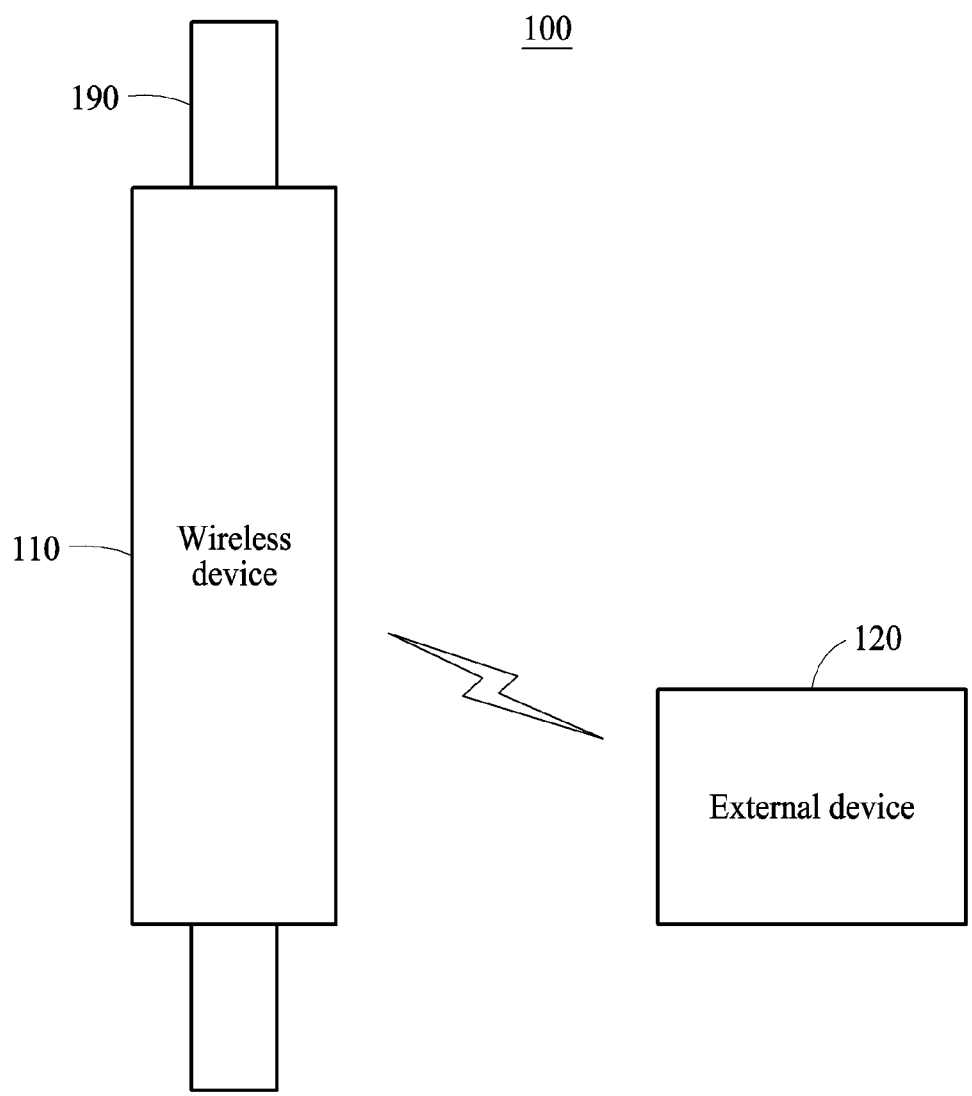
FIGS. 1 and 2 are diagrams illustrating examples of a wireless system.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, descriptions of features that are known in the art may be omitted for increased clarity and conciseness.

The features described herein may be embodied in different forms, and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application.

Throughout the specification, when an element, such as a layer, region, or substrate, is described as being "on," "connected to," or "coupled to" another element, it may be directly "on," "connected to," or "coupled to" the other element, or there may be one or more other elements intervening therebetween. In contrast, when an element is described as being "directly on," "directly connected to," or "directly coupled to" another element, there can be no other elements intervening therebetween.

As used herein, the term "and/or" includes any one and any combination of any two or more of the associated listed items.

Although terms such as "first," "second," and "third" may be used herein to describe various members, components, regions, layers, or sections, these members, components, regions, layers, or sections are not to be limited by these terms. Rather, these terms are only used to distinguish one member, component, region, layer, or section from another member, component, region, layer, or section. Thus, a first member, component, region, layer, or section referred to in examples described herein may also be referred to as a second member, component, region, layer, or section without departing from the teachings of the examples.

Spatially relative terms such as "above," "upper," "below," and "lower" may be used herein for ease of description to describe one element's relationship to another element as shown in the figures. Such spatially relative terms are intended to encompass different orientations of the device in use or operation in addition to the orientation depicted in the figures. For example, if the device in the figures is turned over, an element described as being "above" or "upper" relative to another element will then be "below" or "lower" relative to the other element. Thus, the term "above" encompasses both the above and below orientations depending on the spatial orientation of the device. The device may also be oriented in other ways (for example, rotated 90 degrees or at other orientations), and the spatially relative terms used herein are to be interpreted accordingly.

The terminology used herein is for describing various examples only, and is not to be used to limit the disclosure. The articles "a," "an," and "the" are intended to include the plural forms as well, unless the context clearly indicates otherwise. The terms "comprises," "includes," and "has" specify the presence of stated features, numbers, operations, members, elements, and/or combinations thereof, but do not preclude the presence or addition of one or more other features, numbers, operations, members, elements, and/or combinations thereof.

Unless otherwise defined, all terms, including technical and scientific terms, used herein have the same meaning as commonly understood by one of ordinary skill in the art to which this disclosure pertains based on an understanding of the present disclosure. Terms, such as those defined in commonly used dictionaries, are to be interpreted as having a meaning that is consistent with their meaning in the context of the relevant art and the present disclosure, and are not to be interpreted in an idealized or overly formal sense unless expressly so defined herein.

The features of the examples described herein may be combined in various ways as will be apparent after an understanding of the disclosure of this application. Further, although the examples described herein have a variety of configurations, other configurations are possible as will be apparent after an understanding of the disclosure of this application.

Figure 2:
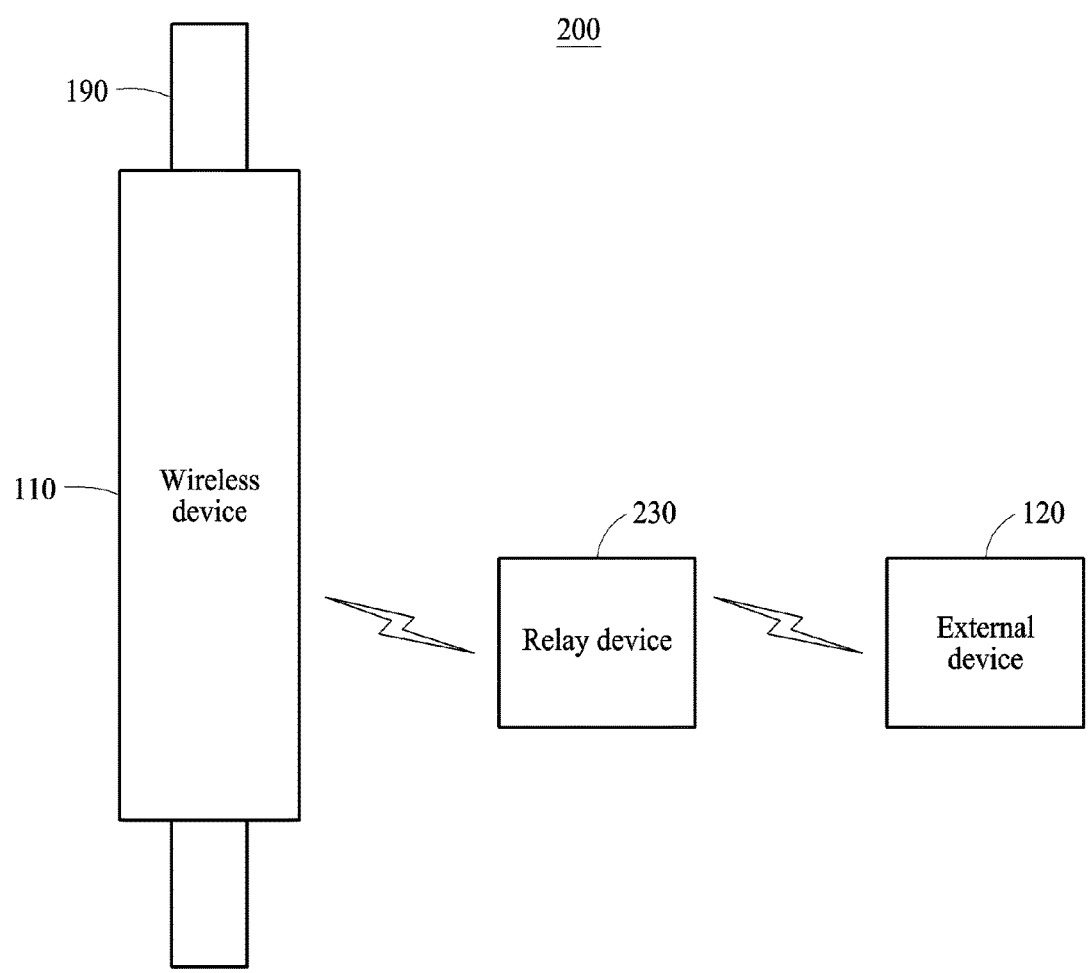

FIGS. 1 and 2 are diagrams illustrating examples of wireless systems 100 and 200, respectively.

Referring to FIG. 1, the wireless system 100 includes a wireless device 110 and an external device 120. Referring to FIG. 2, the wireless system 200 further includes a relay device 230.

The wireless device 110 performs wireless communication with the external device 120. The wireless device 110 establishes direct communication with the external device 120, or establishes communication with the external device 120 through the relay device 230. The wireless device 110 is configured to cover a target 190, and applies an electrical signal to the target 190 or detects an electrical signal from the target 190. The wireless device 110 transfers a signal detected from the target 190 to the external device 120. In addition, the wireless device 110 applies an electrical signal to the target 190 on a periodic basis. The wireless device 110 changes, for example, an electrical signal applying period, an arrangement of electrodes, and a strength, based on a control signal received from the external device 120.

Further, the wireless device 110 wirelessly receives power from either one or both of the external device 120 and the relay device 230. The wireless device 110 charges an embedded battery based on power received from either one or both of the external device 120 and the relay device 230. For example, in a case in which power of the battery is discharged to be less than or equal to a threshold power, the wireless device 110 requests either one or both of the external device 120 and the relay device 230 to wirelessly transmit power. The wireless device 110 is attached to the target 190, or disposed to transmit and receive power through a magnetic field direction that is the same as a magnetic field direction of the relay device 230. Through a mutual resonance formed between the relay device 230 and a coil, the wireless device 110 may perform a wireless power transfer or a wireless power transmission.

The relay device 230 relays communication between the wireless device 110 and the external device 120. The relay device 230 performs information exchanges between the wireless device 110 and the external device 120. For example, the relay device 230 receives, from the wireless device 110, an electrical signal detected by the wireless device 110 and transfers the received electrical signal to the external device 120. In another example, the relay device 230 transfers, to the wireless device 110, information or an instruction received from the external device 120.

The relay device 230 is worn on an object associated with the target 190. The relay device 230 is attached to a portion of the object that is adjacent to the target 190. The object is, for example, a human being and an animal, and the target 190 may be a nerve. The portion adjacent to the target 190 may be skin adjacent to a vagus nerve. The nerve may be a vagus nerve. In such a case, the wireless device 110 applies an electrical signal to the vagus nerve within a range of a voltage, a current, and power that does not cause damage to a human body to stimulate the vagus nerve.

In addition, the relay device 230 provides the wireless device 110 with power charged in the battery. A size of the wireless device 110 may be relatively smaller than a size of the relay device 230, and a capacity of the battery may also be relatively small. In response to a request for a wireless power transfer being received from the wireless device 110, the relay device 230 provides power to the wireless device 110 to charge the battery of the wireless device 110. The relay device 230 charges the battery of the wireless device 110 to extend an operating time of the wireless device 110. A detailed structure of the relay device 230 will be described hereinafter with reference to FIG. 3.

The external device 120 is, for example, a device configured to collect information received from the wireless device 110 or transfer, to the wireless device 110, a command or an instruction to control an operation of the wireless device 110. In addition, the external device 120 wirelessly provides power to either one or both of the wireless device 110 and the relay device 230. For example, the external device 120 processes information received from the wireless device 110, and outputs a result of the processing as visual information and auditory information.

According to an example, the wireless device 110 and the relay device 230 are produced to be smaller in size based on an arrangement of the coil, discrete elements, and embedded elements. In addition, the wireless device 110 and the relay device 230 may perform wireless communication and wireless charging more effectively based on a direction in which the coil included in the wireless device 110 and the relay device 230 is arranged.

When the wireless device 110 is inserted in the object and attached to the target 190, and the relay device 230 is attached to the object, the wireless device 110 and the relay device 230 may have a high transmission efficiency with a small size, using a structure in which coil resonance directions are mutually arranged. In a case in which the object is a human body, the wireless device 110 may be inserted inside the human body from a surface of the human body, and the wireless device 230 may be attached outside the surface of the human body.

According to an example, the wireless device 110 continuously applies an electrical signal to the target 190, for example, a human nerve, to treat a patient suffering from a neurotic disorder such as epilepsy. In addition, the wireless device 110 may apply an electrical signal to the target 190 to relieve or prevent a chronic pain from, for example, rheumatoid arthritis. Further, the relay device 230 may have a high power transmission efficiency for the wireless device 110, without a need to cover a circumference of the object, for example, a neckline, by the relay device 230.

Figure 3:
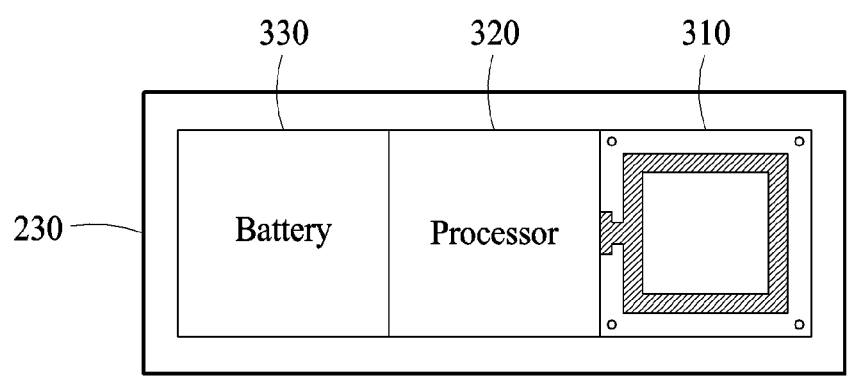
FIG. 3 is a diagram illustrating an example of a relay device.

FIG. 3 is a diagram illustrating an example of the relay device 230.

Referring to FIG. 3, the relay device 230 includes a coil 310, a processor 320, and a battery 330. The relay device 230 is formed of flexible materials, and thus can be closely attached, in a form of a bandage, to a curved surface of an object.

The coil 310 is designed to have a resonance direction matching a resonance direction of a wireless device inserted in the object. The coil 310 forms a mutual resonance with respect to a coil of the wireless device. For example, the coil 310 is designed to have a resonant frequency matching a resonant frequency of the coil of the wireless device.

The processor 320 is disposed on a flexible substrate, and controls an operation of the relay device 230. For example, the processor 320 receives power from an external device through the coil 310 and charges the battery 330. The processor 320 transfers power charged in the battery 330 to the wireless device through the coil 310.

The battery 330 is formed of a flexible material, and provides power to each module of the relay device 230. For example, in response to power of the battery 330 being consumed, the relay device 230 is replaced by a new relay device by a user. Thus, the user may conveniently replace the relay device 230, which is attached to an external surface of the object, without replacing the battery 330 of the wireless device 110, which is inserted in the object.

Figure 4:
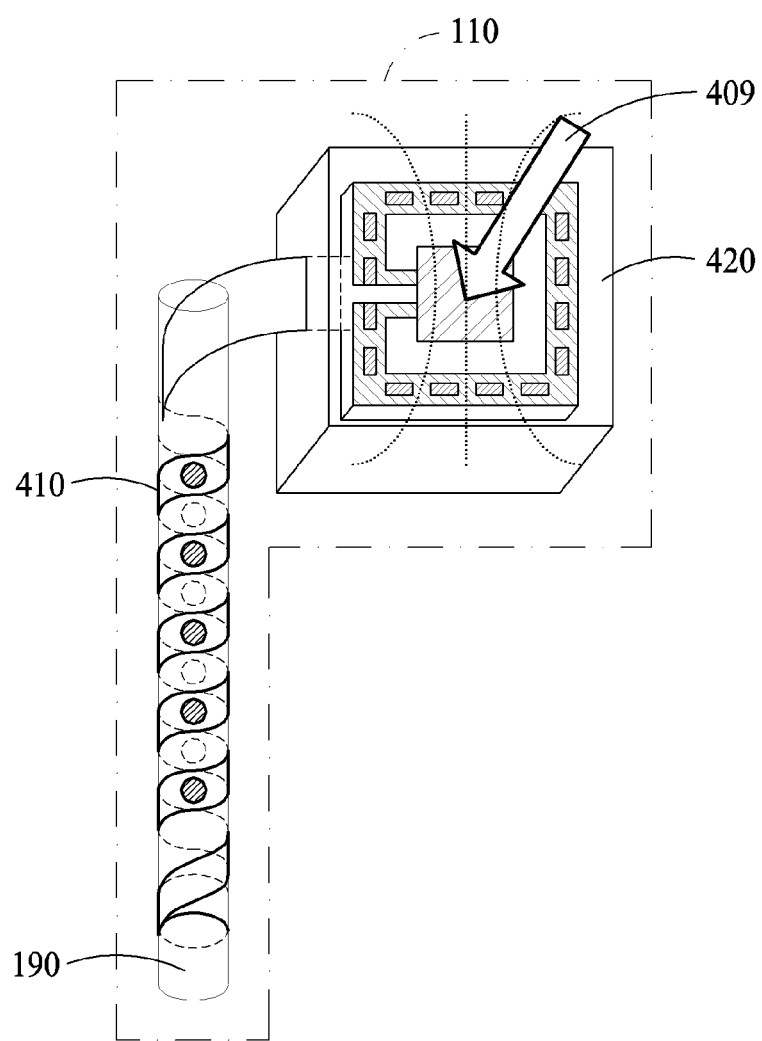
FIG. 4 is a diagram illustrating an example of a wireless device.

FIG. 4 is a diagram illustrating an example of the wireless device 110.

Referring to FIG. 4, the wireless device 110 includes an electrode device 410 and a communication device 420.

The electrode device 410 includes electrodes arranged to cover a target 190. Channels may be allocated to the electrodes. The channels include, for example, a sensing channel used to sense or detect an electrical signal and a stimulating channel used to apply an electrical signal. Thus, the electrode device 410 may simultaneously perform an operation of sensing or detecting an electrical signal from the target 190 and an operation of applying an electrical signal to the target 190 through different channels.

The communication device 420 includes a coil that may be resonant along with a relay device (e.g., the relay device 230) present outside an object. For example, the coil 310 included in the relay device 230 and the coil included in the communication device 420 are designed to have a same or similar resonant frequency. In addition, the coil of the communication device 420 may form a resonance direction 409 that is the same as that of the relay device 230. Elements may be arranged in an upper space and a lower space from the coil of the communication device 420, within a limited form factor. A housing of the wireless device 110 is coated with a water-repellent or water-proof coating. The housing of the wireless device 110 is formed of a biocompatible material, and packages the wireless device 110. An interface of the electrode device 410, for example, a neural interface, is disposed to cover the target 190, for example, a nerve, through a linear arrangement of the electrodes. An electrode of the neural interface of the electrode device 410 is arranged to be in contact with the target 190.

Figure 5:
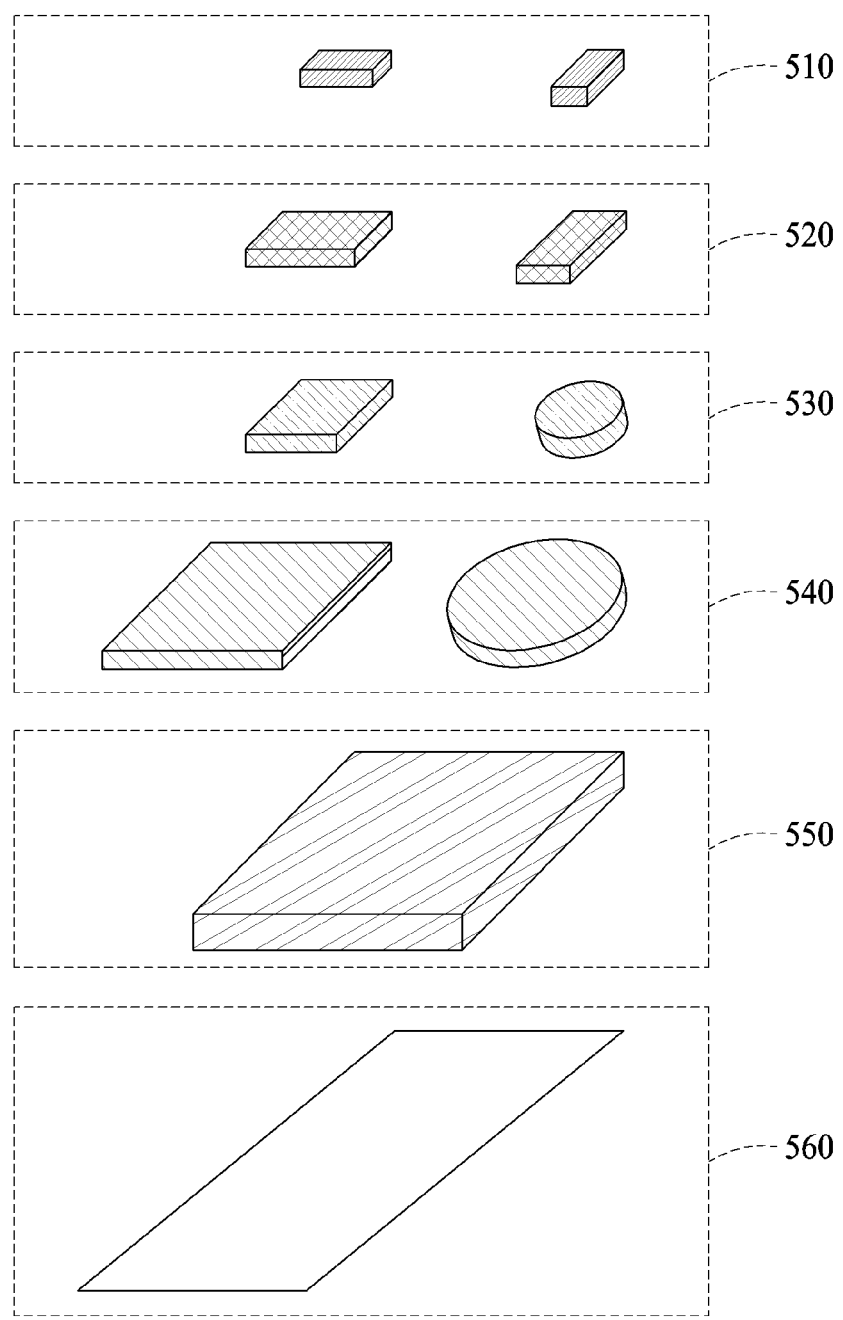
FIG. 5 is a diagram illustrating examples of elements included in a wireless device.

FIG. 5 is a diagram illustrating examples of elements included in the wireless device 110. Elements included in the wireless device 110 may be classified by a function and a size of each of the components.

Referring to FIG. 5, a discrete element 510 is an element arranged on a coil and connected to a chip through a vertical interconnect access (via). In one example, the discrete element 510 is a passive element configured to separate voltages of circuits in the chip, which includes a processor. The discrete element 510 is, for example, a capacitor, an inductor, and a resistor connected to the chip, which includes the processor, through the via. A size of the discrete element 510 is less than or equal to, for example, 0.6×0.3 millimeters (mm).

An embedded element 520 is an element disposed in a layer distinguished from a layer including the coil and a layer including the processor, and connected to the processor through the via. A size of the embedded element 520 is between, for example, 2×1.6 mm and 1×0.5 mm.

An electrode contact 530 is a contact connected to an electrode. For example, the electrode contact 530 is formed of a conductive metal material. A size of the electrode contact 530 may be less than or equal to, for example, 1×1 mm.

A battery contract 540 is a contact connected to a battery. For example, the battery contact 540 is formed of a conductive metal material. The battery contact 540 may be less than or equal to, for example, 2×2 mm.

A chip package 550 is a chip configured to perform various functions. The chip includes, for example, a communication-related circuit, an electrode-related circuit, and a battery-related circuit. The circuits included in the chip will be described in detail with reference to FIGS. 13 and 14. A size of the chip package 550 may be less than or equal to, for example, 3×3 mm.

A substrate 560 is an element on which the coil, the discrete element 510, the embedded element 520, the electrode contact 530, the battery contact 540, and the chip package 550 are disposed. For example, the substrate 560 is formed of a biocompatible and flexible material. A size of the substrate 560 may be less than or equal to, for example, 5×5 mm in a communication device, and may be between 2×30 mm and 2×50 mm in an electrode device.

According to an example, the wireless device 110 may be smaller in size by using a structure in which the elements described above are stacked. For example, the discrete element 510 is arranged on the coil and a signal received through the coil is transferred to the processor through the via, and thus a mounting space may be provided. In addition, the chip package 550 and the embedded element 520 are disposed in a core area of the communication device 420. The coil is disposed around the core area, and the core area is laterally spaced from the coil by a threshold distance. For example, the core area corresponds to an interior region of an area bounded by the coil. The mounting space may be embodied as a three-dimensional (3D) space. The chip package 550 will also be referred to as a chip.

Figure 6:
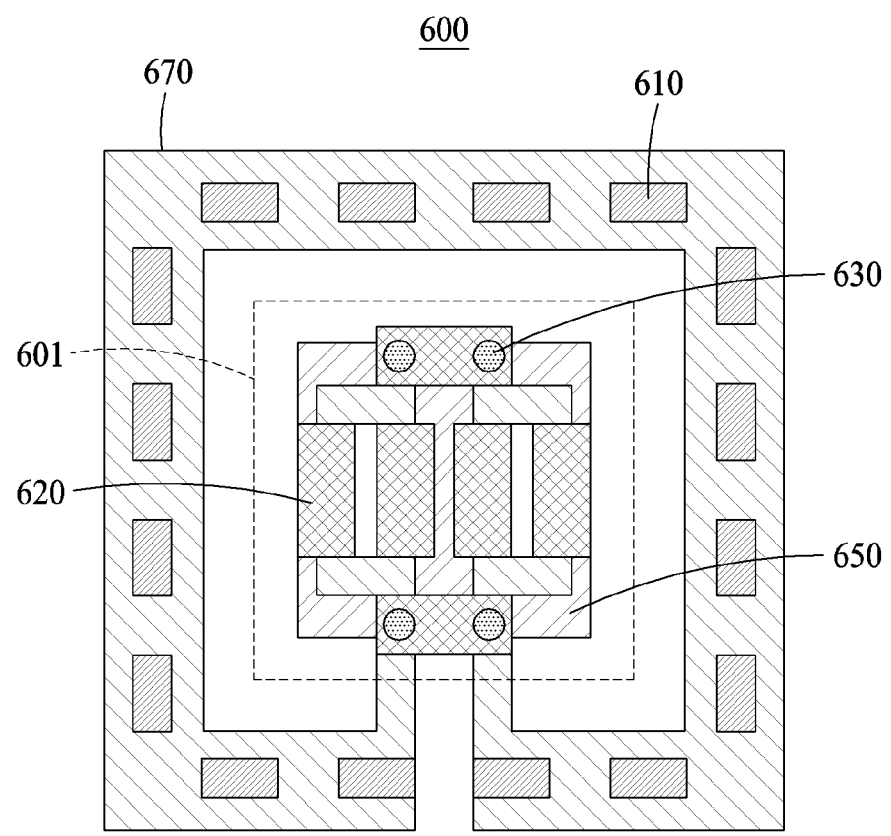
FIGS. 6 through 8 are diagrams illustrating an example of a structure of a communication device.
Figure 7:
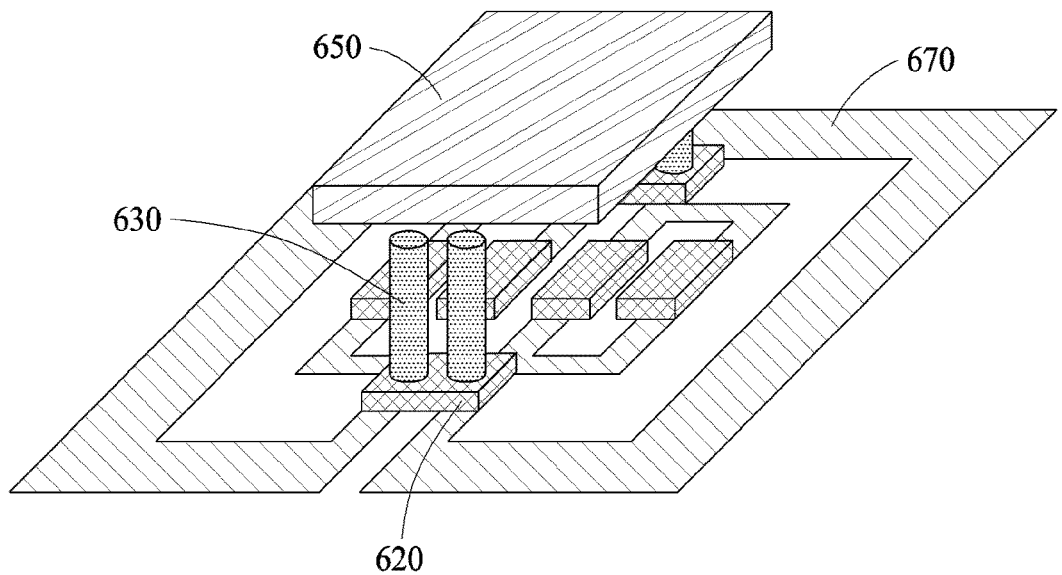
Figure 8:
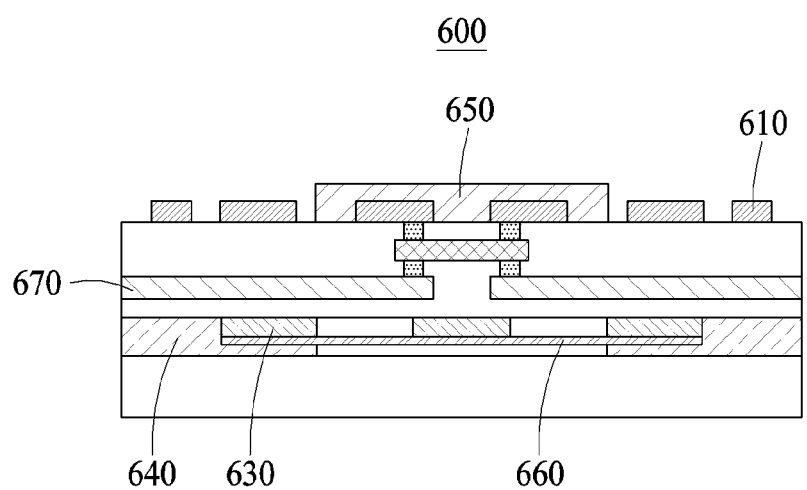

FIGS. 6 through 8 are diagrams illustrating an example of a structure of a communication device 600.

FIG. 6 is a top view of the communication device 600, FIG. 7 is a perspective view of the communication device 600, and FIG. 8 is a front view of the communication device 600.

Referring to FIGS. 6 through 8, discrete elements 610, a chip 650, and embedded elements 620 are disposed in an upper layer that is above a layer including a coil 670 of the communication device 600. An electrode contact 630, a battery contact 640, and a substrate 660 are disposed in a lower layer that is below the layer including the coil 670. For example, a processor included in the chip 650 is disposed in a layer distinguished from the coil 670. In other words, the processor included in the chip 650 and the coil 670 are disposed in different layers.

In one example, the discrete elements 610 are arranged on the coil 670 in a layer, for example, the upper layer, that is distinguished from the layer including the coil 670. For example, the discrete elements 610 are arranged in an outer edge ring area excluding a core area 601, around which the coil 670 is disposed, in the layer distinguished from the coil 670. Thus, the discrete elements 610 may be less affected by a magnetic field or an electric field that is formed by the coil 670 in the core area 601. For example, the discrete elements 610 are arranged on the coil 670 to be separate from each other by a preset or specified distance. In addition, the discrete elements 610 are arranged along the coil 670 at a preset or specified interval, for example, an interval obtained by dividing a circumference length of the coil 670 by a number of the discrete elements 610.

The chip 650, including the processor, is disposed in the core area 601.

The embedded elements 620 are disposed in a layer distinguished from the layer including the coil 670 and the layer including the processor. For example, in a case in which an embedded element having a large size or a large area is to be disposed on the coil 670, the embedded element is disposed in the core area 601 in a layer under a layer including the chip 650.

In one example, the embedded elements 620 include an isolated network circuit configured to separate a signal of a first bandwidth and a signal of a second bandwidth. The embedded elements 620 also include a first capacitor that is connected to a first partial coil in the coil 670 to receive the signal of the first bandwidth, and a second capacitor that is connected to a second partial coil in the coil 670 to receive the signal of the second bandwidth. In this example, the first partial coil and the second partial coil share at least one loop.

For example, the isolated network circuit blocks an inflow of the signal of the second bandwidth into a first transceiver circuit configured to transmit and receive the signal of the first bandwidth through the first partial coil. Similarly, the isolated network circuit blocks an inflow of the signal of the first bandwidth into a second transceiver circuit configured to transmit and receive the signal of the second bandwidth through the second partial coil. For example, the isolated network circuit includes a band-stop filter at a front end of the first transceiver circuit to block the signal of the second bandwidth, and a band-stop filter at a front end of the second transceiver circuit to block the signal of the first bandwidth.

The second bandwidth is a bandwidth allocated for a wireless power transfer, and the first bandwidth is a bandwidth allocated for wireless communication. For example, the second bandwidth indicates a frequency bandwidth that is lower than the first bandwidth. The bandwidths are not limited to the preceding example, and the second bandwidth and the first bandwidth may vary based on a design.

The electrode contact 630, the battery contact 640, and the substrate 660, which are disposed in the lower layer below the layer including the coil 670, are connected to the chip 650 through a via. The electrode contact 630, the battery contact 640, and the substrate 660 transmit and receive a signal with the chip 650 through the via.

Figure 9:
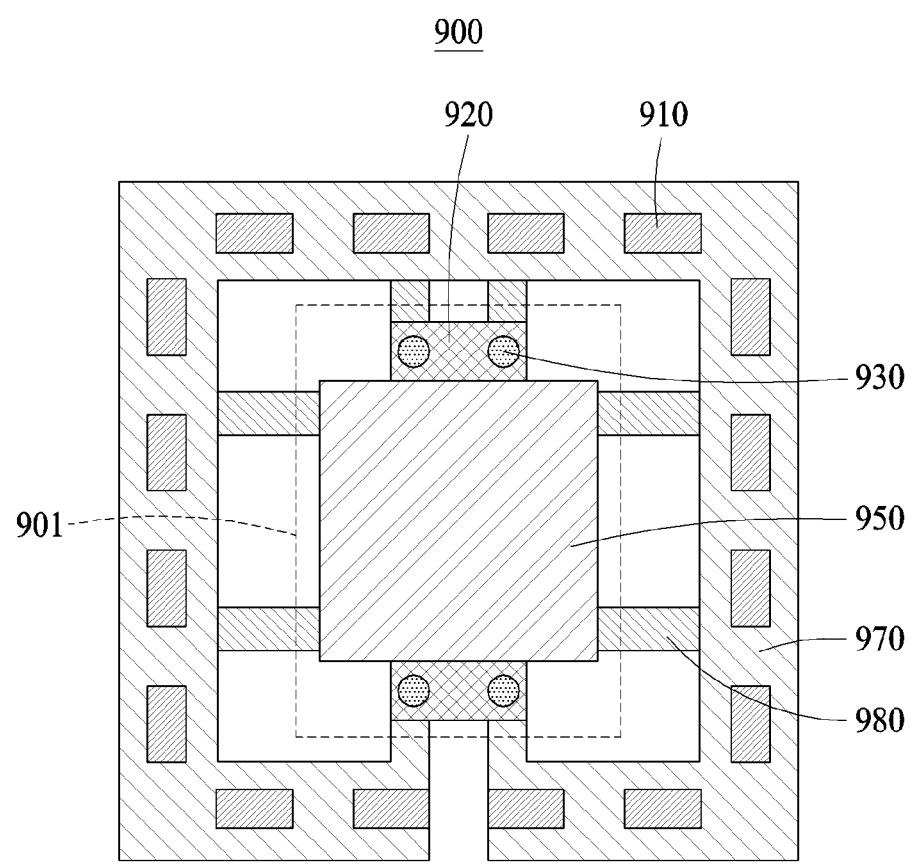
FIGS. 9 through 11 are diagrams illustrating another example of a structure of a communication device.
Figure 10:
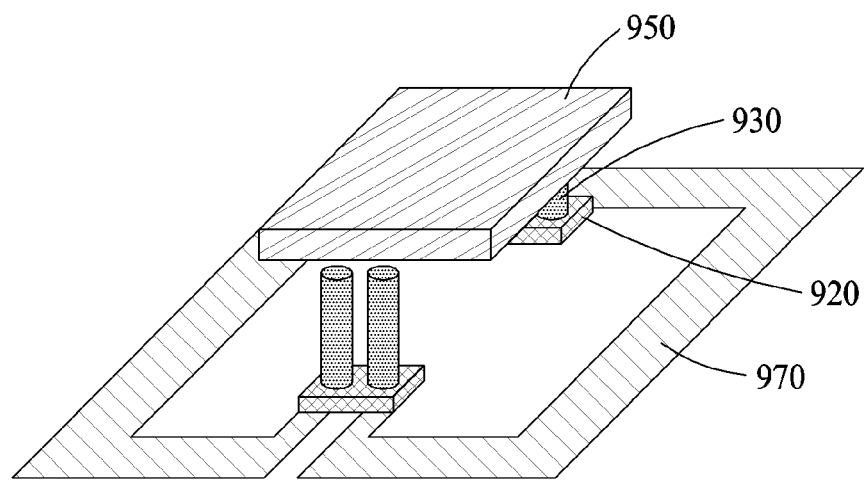
Figure 10:
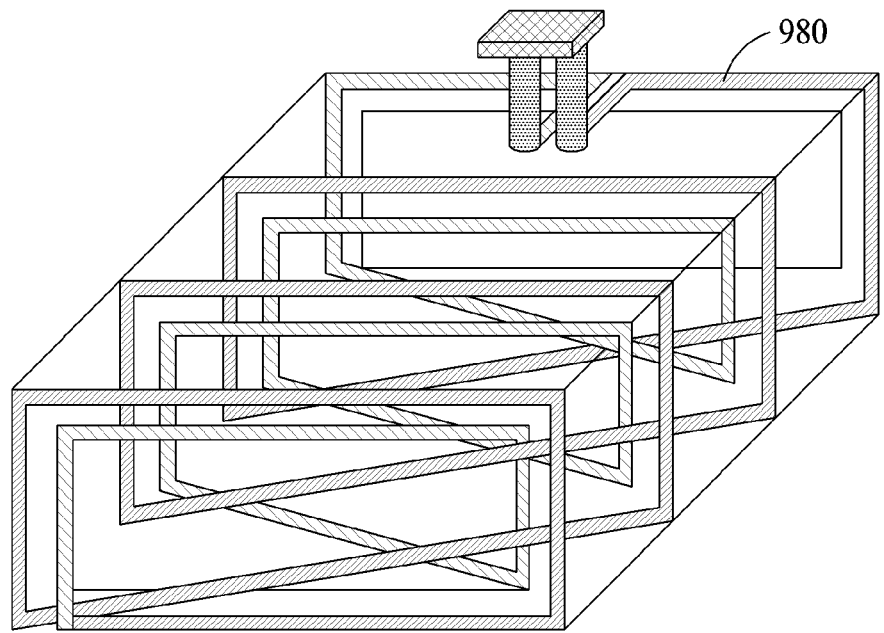
Figure 11:
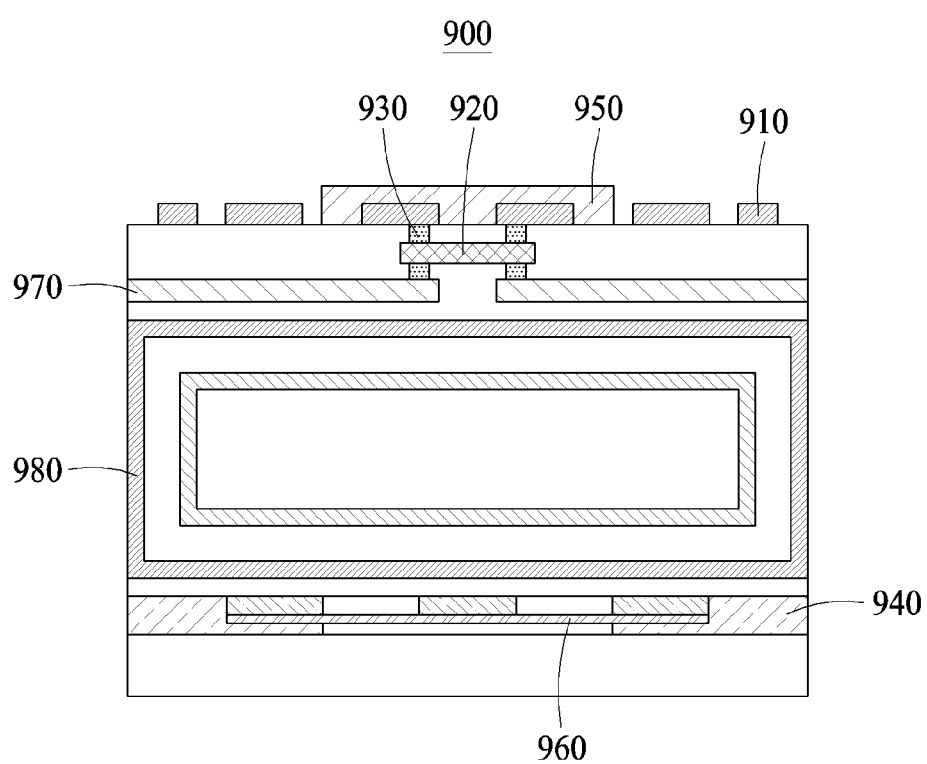

FIGS. 9 through 11 are diagrams illustrating another example of a structure of a communication device 900.

FIG. 9 is a top view of the communication device 900, FIG. 10 is a perspective view of the communication device 900, and FIG. 11 is a front view of the communication device 900.

Elements disposed in an upper layer above a coil in the communication device 900, for example, discrete elements 910, embedded elements 920, an electrode contact 930, and a chip 950 illustrated in FIGS. 9 through 11, may be arranged similarly to the discrete elements 610, the embedded elements 620, the electrode contact 630, and the chip 650 as illustrated in FIGS. 6 through 8.

The coil includes a first partial coil 970 configured to resonate in a first bandwidth and a second partial coil 980 configured to resonate in a second bandwidth different from the first bandwidth.

The first partial coil 970 and the second partial coil 980 are designed to have different resonance directions. For example, a resonance direction of the first partial coil 970 is orthogonal to a resonance direction of the second partial coil 980. In one example, the first partial coil 970 includes a loop configured to generate an electric field, E-field, in a first direction and the second partial coil 980 includes a loop configured to generate a magnetic field, H-field, in a second direction. The first direction and the second direction may be orthogonal to each other. In addition, the second partial coil 980 includes a loop configured to generate the E-field in the first direction orthogonal to the second direction, while generating the H-field in the second direction. Thus, the first partial coil 970 and the second partial coil 980 may be disposed to enable a wireless power transfer and wireless communication in a same direction without hindering the H-field and the E-field of each.

For example, as illustrated in FIG. 9, the first partial coil 970 includes planar loops, and the second partial coil 980 includes double helical loops. In addition, as illustrated in FIGS. 10 and 11, the second partial coil 980 is disposed to occupy a 3D space below a layer including the first partial coil 970.

The battery contact 940 and the substrate 960 are disposed in a layer below the second partial coil 980.

Figure 12:
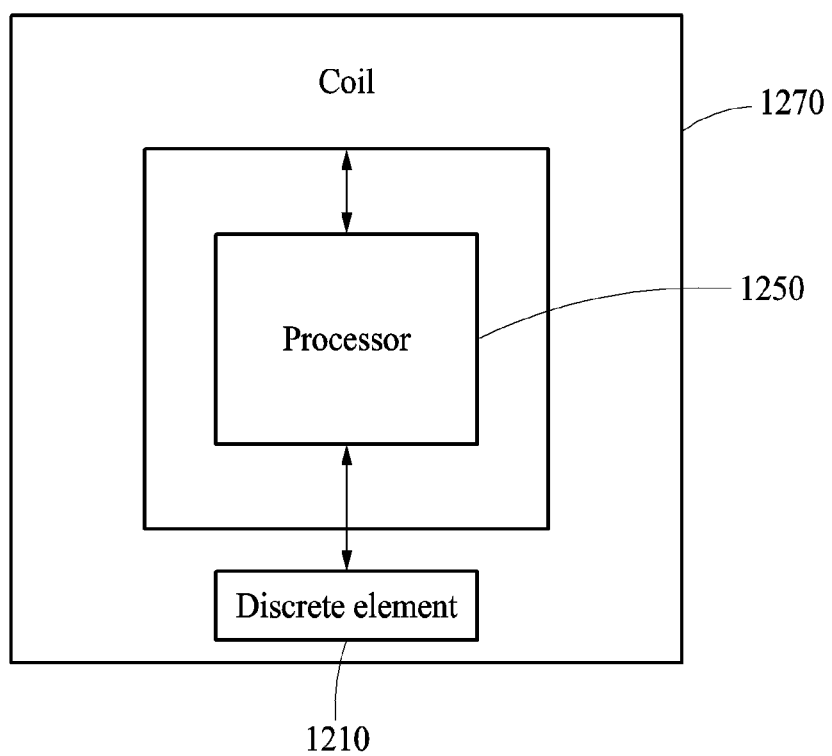
FIGS. 12 through 14 are diagrams illustrating example configurations of communication devices.
Figure 13:
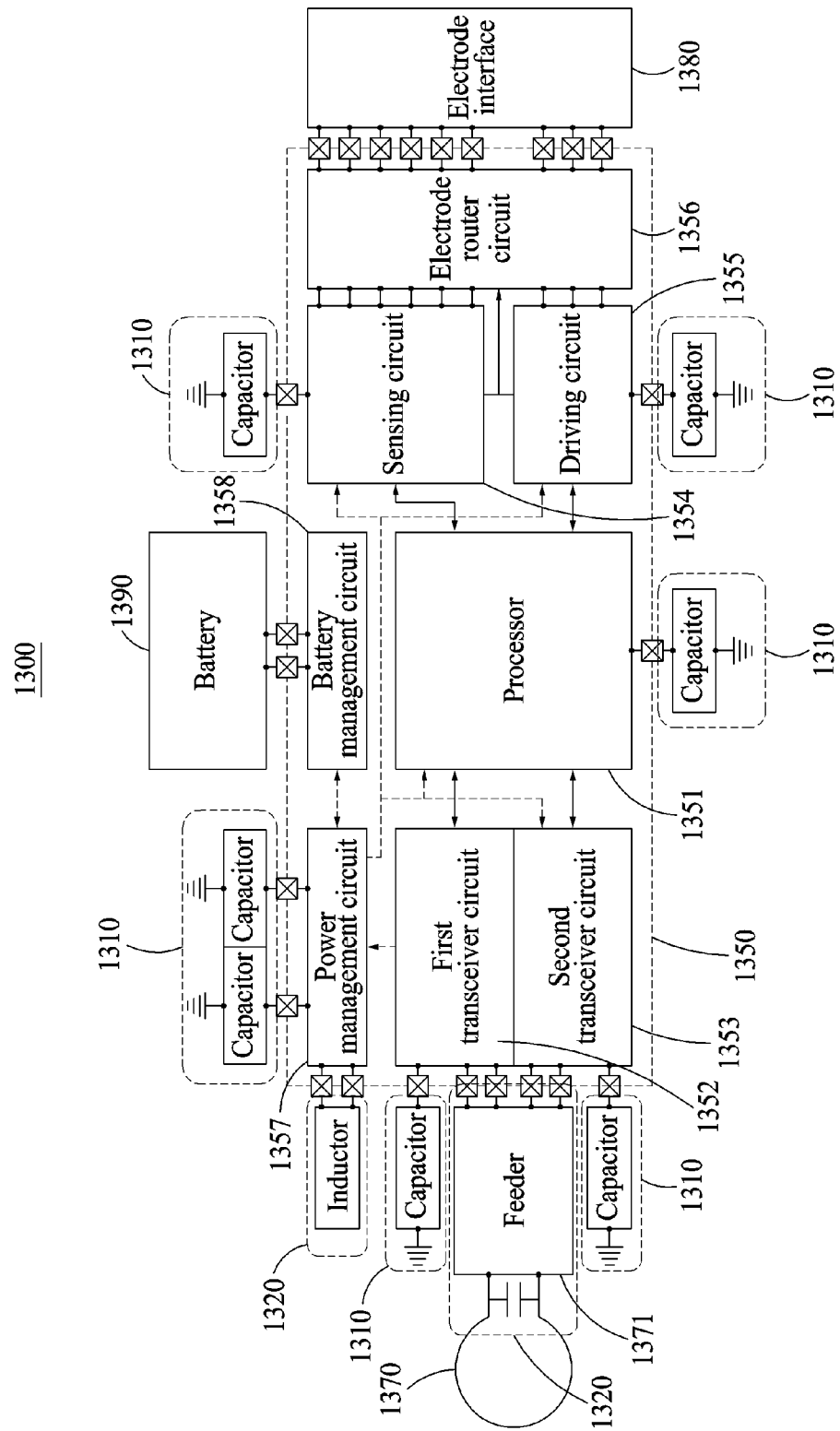
Figure 14:
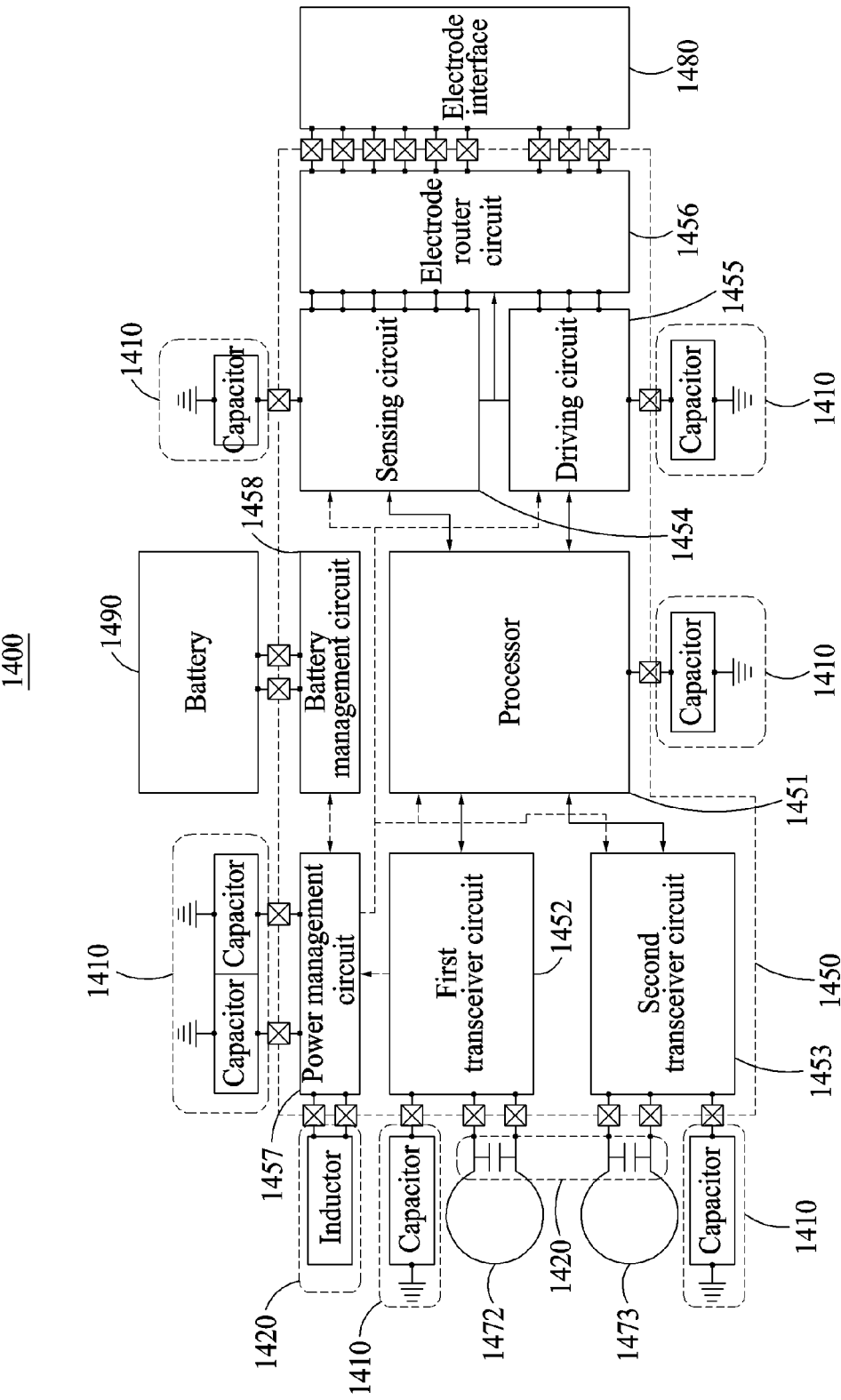

FIGS. 12 through 14 are diagrams illustrating examples of configurations of communication devices.

FIG. 12 is a diagram illustrating a configuration of a communication device 1200.

Referring to FIG. 12, the communication device 1200 includes a discrete element 1210, a processor 1250, and a coil 1270.

The coil 1270 is used to establish wireless communication with either one or both of a relay device and an external device, which is present outside an object, or wirelessly receive power from either one or both of the relay device and the external device.

The processor 1250 is disposed in a core area around which the coil 1270 is disposed, and establishes communication with the external device through the coil 1270. The processor 1250 is connected to electrodes arranged in a form covering a target, and receives an electrical signal from at least one of the electrodes or provides an electrical signal to at least one of the electrodes.

The discrete element 1210 is arranged on the coil 1270 and connected to the processor 1250 through a via. As described above, the discrete element 1210 is disposed in an area of the coil 1270 that is in a layer distinguished from the coil 1270, and thus a mounting space may be secured in the communication device 1200. As illustrated in FIG. 12, the discrete element 1210 is arranged in the layer distinguished from the coil 1270 in an area including the coil 1270, for example, a planar area. For example, the area including the coil 1270 is provided in a form of an outer edge ring, and the discrete element 1210 is arranged in an outer edge ring area in the layer distinguished from the coil 1270.

FIG. 13 is a diagram illustrating a circuit of a communication device 1300, which corresponds to the communication device 600 illustrated in FIGS. 6 through 8.

Referring to FIG. 13, the communication device 1300 includes discrete elements 1310, embedded elements 1320, a chip 1350, a coil 1370, an electrode interface 1380, and a battery 1390.

The discrete elements 1310 separate voltages of circuits in the chip 1350 including a processor 1351. For example, the discrete elements 1310 decouple noise of a power supply, for example, a power management circuit 1357, from the circuits. As described above, the discrete elements 1310 are arranged on the coil 1370 and connected to the chip 1350 through a via. In FIGS. 13 and 14,  indicates a connection through the via.

The embedded elements 1320 include an inductor connected to the power management circuit 1357 in the chip 1350. In addition, the embedded elements 1320 include a capacitor configured to set a resonant frequency of a feeder 1371 configured to feed power to the coil 1370 and a resonant frequency of the coil 1370.

The chip 1350 includes the processor 1351, a first transceiver circuit 1352, a second transceiver circuit 1353, a sensing circuit 1354, a driving circuit 1355, an electrode router circuit 1356, the power management circuit 1357, and a battery management circuit 1358.

The first transceiver circuit 1352 transmits and receives a signal of a first bandwidth through the coil 1370. For example, the first transceiver circuit 1352 transmits and receives the signal of the first bandwidth through a first partial coil of the coil 1370. The second transceiver circuit 1353 transmits and receives a signal of a second bandwidth different from the first bandwidth through the coil 1370. For example, the second transceiver circuit 1353 transmits and receives the signal of the second bandwidth through a second partial coil of the coil 1370. The first partial coil and the second partial coil share at least one loop. As illustrated in FIG. 13, the first transceiver circuit 1352 and the second transceiver circuit 1353 are included in the chip 1350 including the processor 1351. For example, the first transceiver circuit 1352 performs wireless communication through the signal of the first bandwidth, and the second transceiver circuit 1353 wirelessly receives power through the second bandwidth. The wireless communication may be far-field communication, and a wireless power transfer may be near-field communication.

The sensing circuit 1354 detects, through a first electrode, an electrical signal corresponding to a point on an object (e.g., human body) to which the first electrode is attached. The first electrode is an electrode connected to the sensing circuit 1354 through the electrode router circuit 1356 among electrodes included in the electrode interface 1380. The first electrode is also an electrode to which a sensing channel is allocated. The sensing circuit 1354 detects an electrical signal from a target, for example, a human nerve.

The driving circuit 1355 applies, through a second electrode, an electrical signal to a point on the object to which the second electrode is attached. The second electrode is an electrode connected to the driving circuit 1355 through the electrode router circuit 1356 among the electrodes included in the electrode interface 1380. The second electrode is also an electrode to which a stimulating channel is allocated. The driving circuit 1355 applies an electrical signal of a magnitude or amplitude that may not cause damage to the target, for example, a human nerve.

The sensing circuit 1354 and the driving circuit 1355 may be analog front ends (AFEs).

The electrode router circuit 1356 is connected to the electrodes. The electrode router circuit 1356 is included in the chip 1350 including the processor 1351. The electrode router circuit 1356 connects the first electrode among the electrodes to the sensing circuit 1354, and connects the second electrode among the electrodes to the driving circuit 1355.

The power management circuit 1357 is a circuit used to supply power to each of the other circuits of the communication device 1300. For example, the power management circuit 1357 manages power received through the coil 1370 and obtained from the battery 1390, and distributes the power to each of the other circuits.

The battery management circuit 1358 charges or discharges the battery 1390. For example, the battery management circuit 1358 charges the battery 1390 with power obtained through the power management circuit 1357. In addition, the battery management circuit 1358 provides the power management circuit 1357 with power obtained from the battery 1390.

FIG. 14 is a diagram illustrating a circuit of a communication device 1400, which corresponds to the communication device 900 illustrated in FIGS. 9 through 11.

Discrete elements 1410, a chip 1450, an electrode interface 1480, and a battery 1490, which are included in a communication device 1400 illustrated in FIG. 14, may be similar to the discrete elements 1310, the chip 1350, the electrode interface 1380, and the battery 1390, which are included in the communication device 1300 illustrated in FIG. 13. In addition, a processor 1451, a sensing circuit 1454, a driving circuit 1455, an electrode router circuit 1456, a power management circuit 1457, and a battery management circuit 1458, which are included in the chip 1450 illustrated in FIG. 14, may be similar to the processor 1351, the sensing circuit 1354, the driving circuit 1355, the electrode router circuit 1356, the power management circuit 1357, and the battery management circuit 1358, which are included in the chip 1350 illustrated in FIG. 13.

Referring to FIG. 14, the communication device 1400 includes a first partial coil 1472 and a second partial coil 1473. The first partial coil 1472 and the second partial coil 1473 are connected to a first transceiver circuit 1452 and a second transceiver circuit 1453, respectively. The first transceiver circuit 1452 transmits and receives a signal of a first bandwidth, and the second transceiver circuit 1453 transmits and receives a signal of a second bandwidth.

One embedded element among embedded elements 1420 is a first capacitor connected to the first partial coil 1472 and configured to set a resonant frequency of the first partial coil 1472. Another embedded element among the embedded elements 1420 is a second capacitor connected to the second partial coil 1473 and configured to set a resonant frequency of the second partial coil 1473. In addition, yet another embedded element among the embedded elements 1420 is an inductor connected to the power management circuit 1457.

Figure 15:
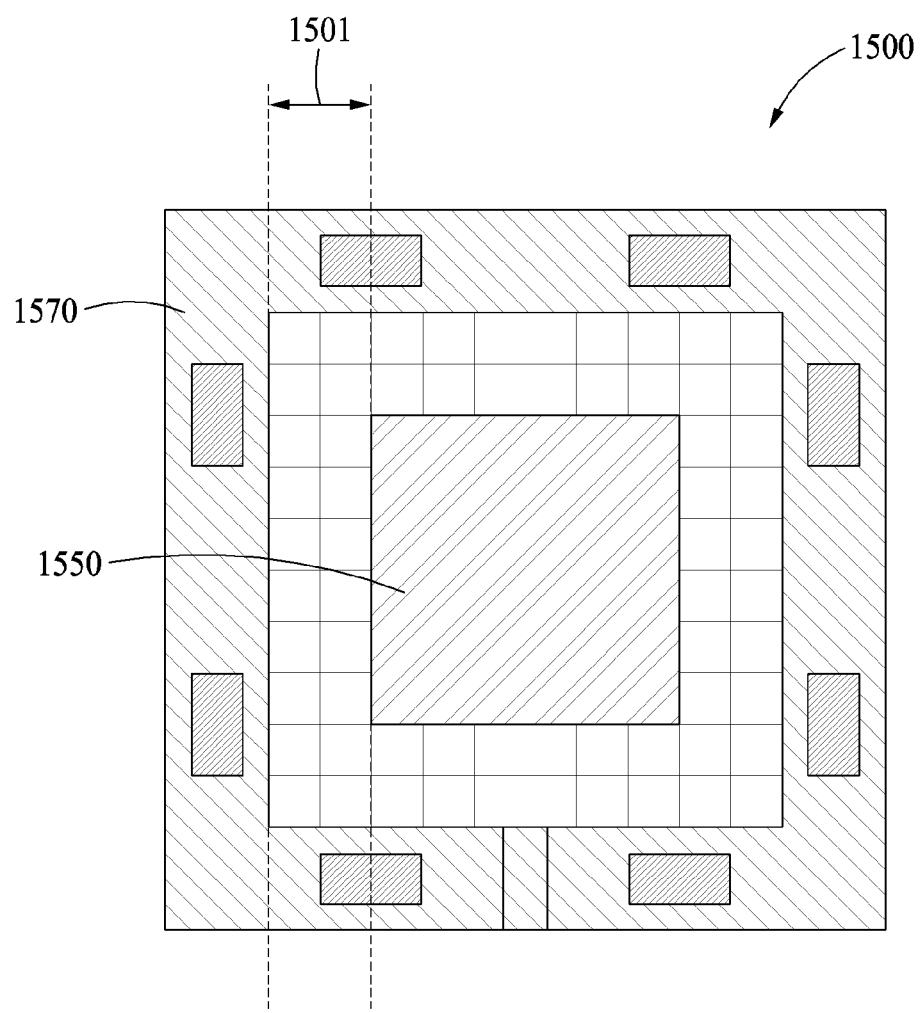
FIG. 15 is a diagram illustrating an example of a distance between a coil and a chip of a communication device.

FIG. 15 is a diagram illustrating an example of a distance between a coil 1570 and a chip 1550 of a communication device 1500.

Referring to FIG. 15, the chip 1550 including a processor is spaced from the coil 1570 by a distance 1501 that is greater than or equal to a threshold distance. In response to the distance 1501 between the coil 1570 and the chip 1550 increasing, a radiation efficiency of the coil 1570 may be improved.

For example, in a case in which the distance 1501 between the coil 1570 and the chip 1550 is 1 millimeter (mm), the radiation efficiency may be degraded by approximately 2 decibels (dB) compared to a structure in which only the coil 1570 is arranged. In a case in which the distance 1501 between the coil 1570 and the chip 1550 is less than 1 mm, the radiation efficiency may be degraded by approximately 5 dB compared to the structure in which only the coil 1570 is arranged.

In addition, an arrangement of discrete elements on the coil 1570 may reduce a degradation of the radiation efficiency of the coil 1570. For example, as illustrated in FIG. 15, eight discrete elements each having a length of 1 mm and a width of 0.05 mm are arranged in an area of the coil 1570, and the radiation efficiency is degraded by only −0.4 dB.

Thus, by arranging discrete elements in another layer distinguished from the coil 1570 in a planar area corresponding to the coil 1570, the radiation efficiency of the coil 1570 may be minimally degraded and the communication device may have a structure for which a space utilization is maximized.

Figure 16:
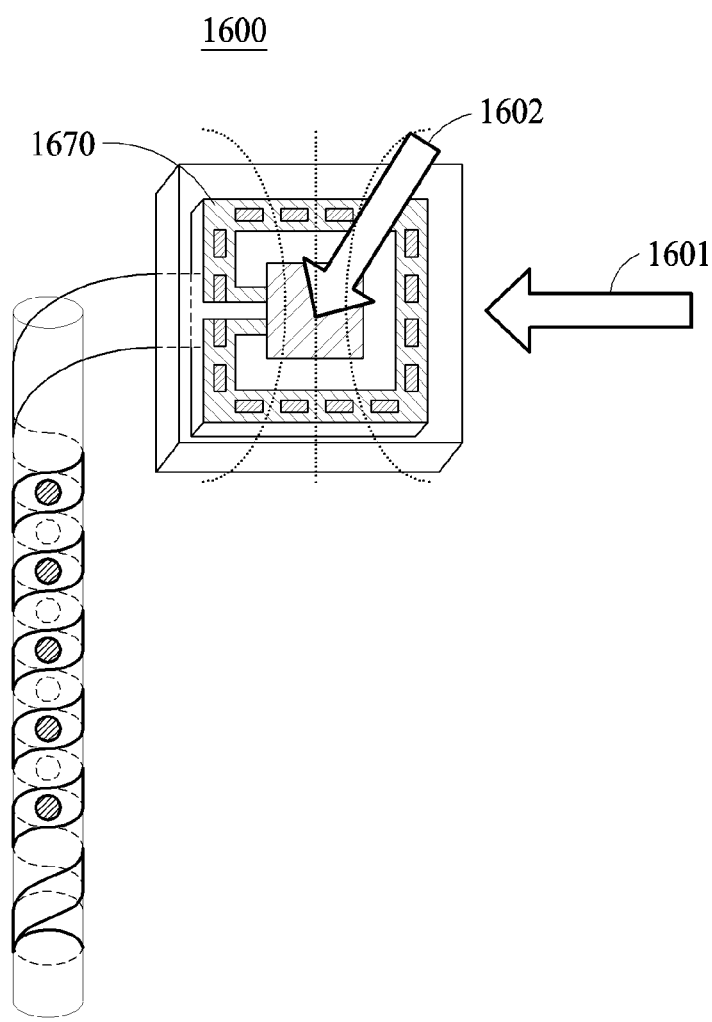
FIGS. 16 and 17 are diagrams illustrating examples of structures of coils communication devices.
Figure 17:
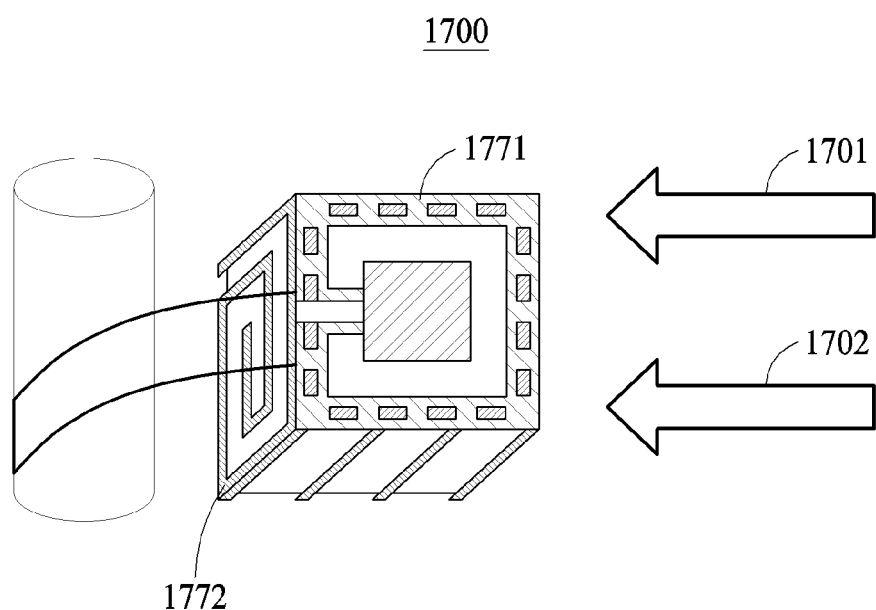

FIGS. 16 and 17 are diagrams illustrating examples of structures of coils of communication devices.

Referring to FIG. 16, a coil 1670 of a communication device 1600 includes a first partial coil and a second partial coil, and the first partial coil and the second partial coil share at least one loop.

In one example, the first partial coil and the second partial coil are designed to have a same resonance axis, and a direction of a magnetic field, for example, a second direction 1602 illustrated in FIG. 16, that is generated by the coil 1670 follows the resonance axis. For example, the first partial coil transmits and receives a signal used for wireless communication, and the wireless communication is established by generating an electric field, E-field, in a first direction 1601. In addition, the second partial coil wirelessly receives power, and the power is wirelessly received by generating a magnetic field, H-field, in the second direction 1602.

As illustrated in FIG. 16, the first partial coil and the second partial coil have the same direction of the magnetic field, for example, the second direction 1602. In this example, the direction of the electric field and the direction of the magnetic field may be orthogonal to each other, and thus the first partial coil may establish the wireless communication through the electric field E-field in the first direction 1601, and the second partial coil may wirelessly receive power through the magnetic field H-field in the second direction 1602. The first direction 1601 and the second direction 1602 may be orthogonal to each other.

Thus, a structure in which the first partial coil and the second partial coil share at least one loop may be designed to be a planar structure to minimize a space. In addition, directions for the wireless communication and the wireless power transfer may be separated, as in the first direction 1601 of the wireless communication and the second direction 1602 of the wireless power transfer.

FIG. 17 is a diagram illustrating a communication device 1700 in which a resonance direction of a first partial coil 1771 and a resonance direction of a second partial coil 1772 are orthogonal to each other.

Referring to FIG. 17, a first partial coil 1771 is configured to be in a planar loop structure, and a second partial coil 1772 is configured to be in a 3D double helical loop structure.

For example, a direction of a magnetic field of the first partial coil 1771 and a direction of a magnetic field of the second partial coil 1772 are designed to be orthogonal to each other. Since a direction of an electric field and a direction of a magnetic field may be orthogonal to each other, the first partial coil 1771 includes a loop configured to generate an electric field, E-field, in a first direction 1701, and the second partial coil 1772 includes a loop configured to generate a magnetic field, H-field, in a first direction 1702. The first partial coil 1771 establishes wireless communication in the first direction 1701, and the second partial coil 1772 wirelessly receives power from the first direction 1702. Thus, a communication device 1700 may perform the wireless communication and a wireless power transfer in the same first directions 1701 and 1702.

Thus, by arranging the direction of the magnetic field and the direction of the electric field as described above, a communication distance and a power transmission efficiency may be improved when the communication device 1700 is inserted in an object, for example, a human body.

Figure 18:
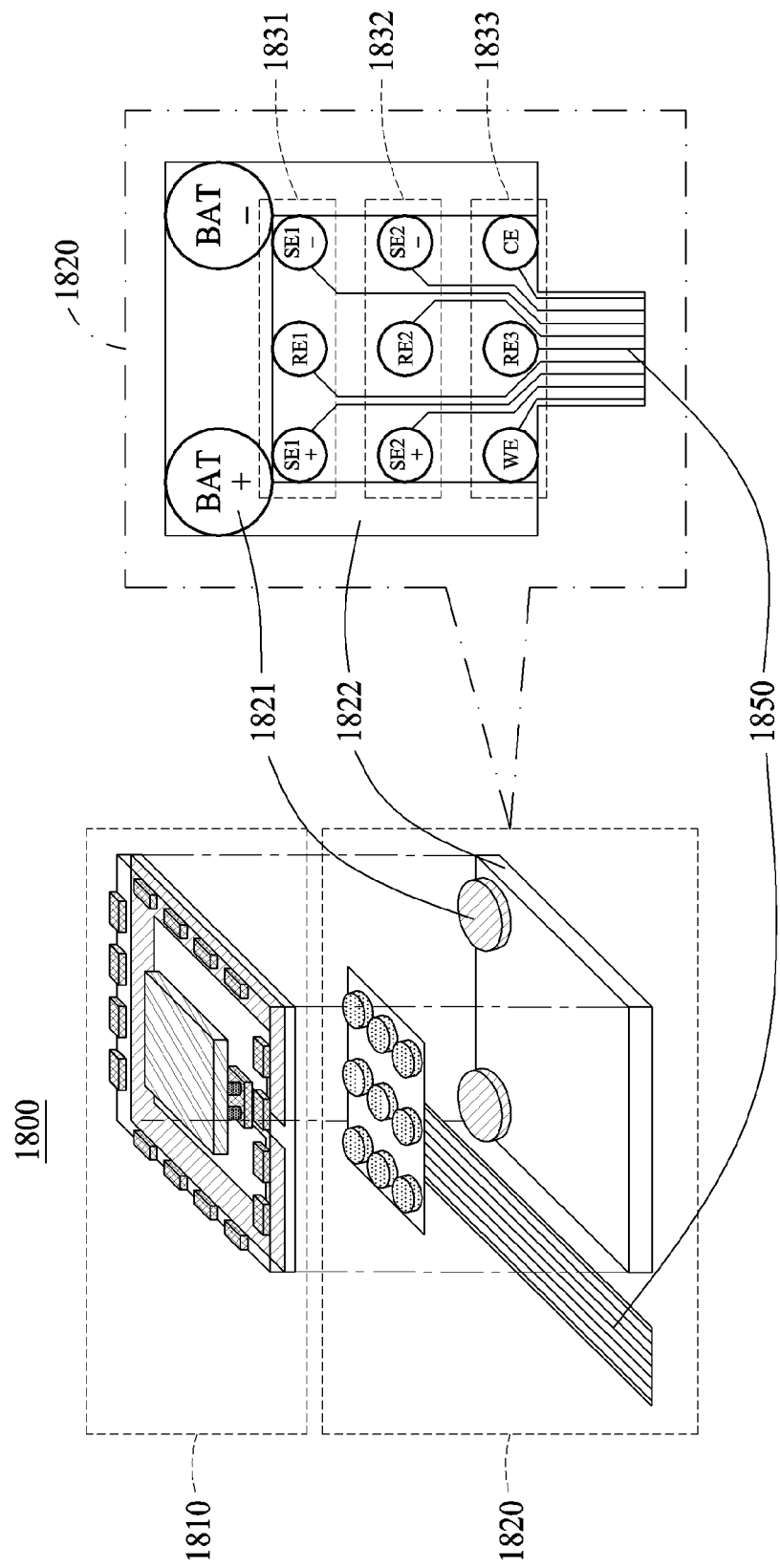
FIGS. 18 and 19 are diagrams illustrating examples of a communication device and an example of an electrode device.
Figure 19:
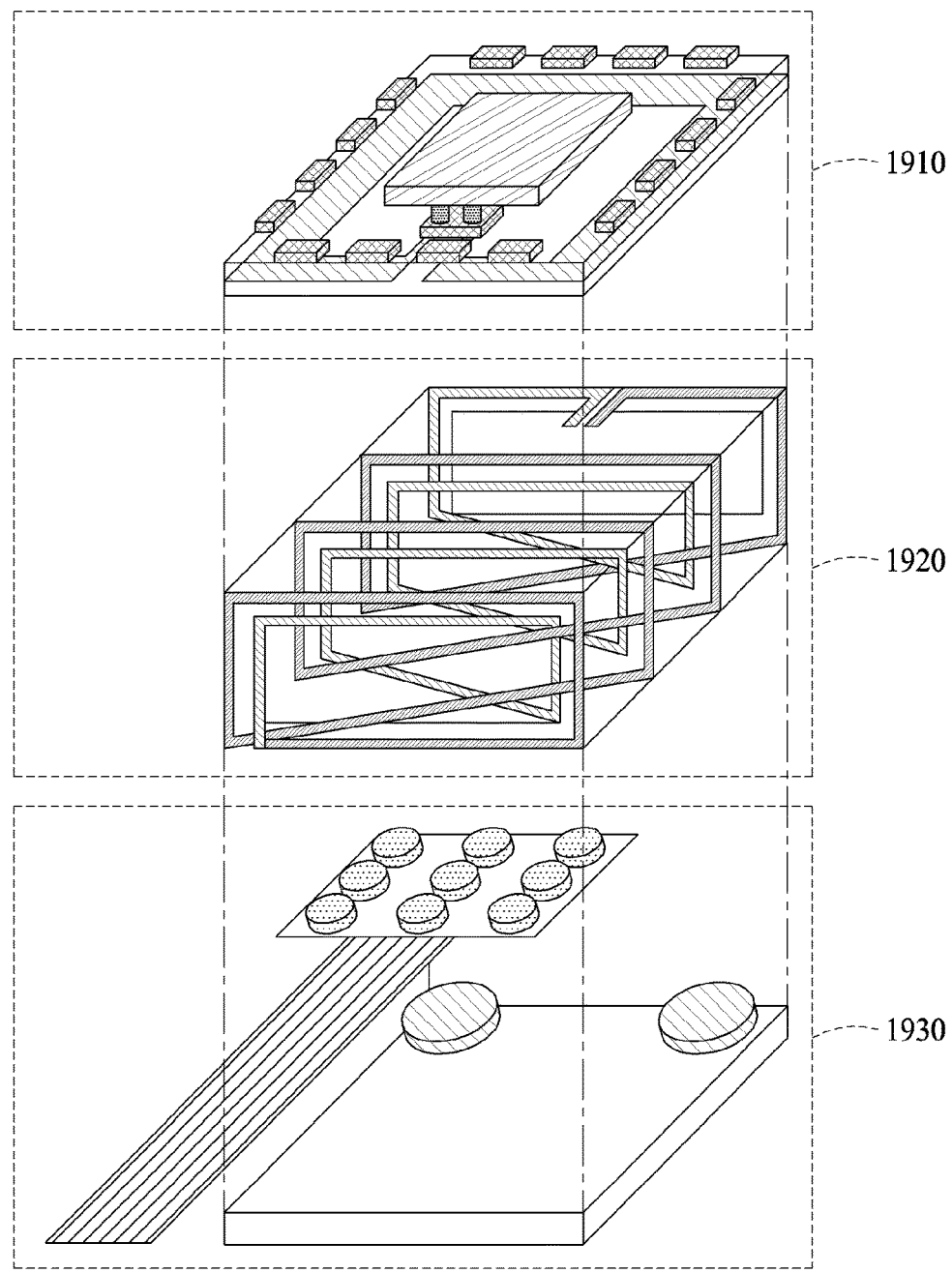

FIGS. 18 and 19 are diagrams illustrating examples of communication devices and an example of an electrode device.

FIG. 18 is a diagram illustrating an example of a wireless device 1800 having a structure in which a communication device 1810 including a coil having a planar structure is integrated with an electrode device 1820.

The communication device 1810 illustrated in FIG. 18 may be configured similarly to the communication device 600 illustrated in FIGS. 6 through 8.

The electrode device 1820 includes a substrate 1850 on which electrodes are arranged, and a battery 1822.

A battery contact 1821 is disposed on the battery 1822. Power of the battery 1822 is transferred to the communication device 1810 through the battery contact 1821. The battery contact 1821 includes a positive contact and a negative contact.

The electrodes are arranged on the substrate 1850. The electrodes are classified based on channels, for example, sensing channels 1831 and 1832, and a stimulating channel 1833.

The sensing channels 1831 and 1832 are channels to detect or sense an electrical signal from a target. The sensing channels 1831 and 1832 include a first sensing channel 1831 and a second sensing channel 1832. Each of the sensing channels 1831 and 1832 includes a positive electrode, a negative electrode, and a reference electrode. Thus, each of the sensing channels 1831 and 1832 may obtain a differential signal. A number of sensing channels is not limited to the example described above, and may vary based on a design.

The stimulating channel 1833 includes a working electrode, a counter electrode, and a reference electrode.

FIG. 19 is a diagram illustrating a communication device 1910 that is configured similarly to the communication device 900 described with reference to FIGS. 9 through 11.

Referring to FIG. 19, a circuit 1910 corresponding to a first partial coil and a circuit 1920 corresponding to a second partial coil are stacked or laminated in sequential order. For example, the circuit 1910 corresponding to the first partial coil including a planar loop is disposed in an upper layer, and the circuit 1920 corresponding to the second partial coil, which includes a double helical loop that has a resonance direction orthogonal to the first partial coil is three-dimensionally disposed in a middle layer. An electrode device 1930 is disposed in a lower layer. The electrode device 1930 may be configured similarly to the electrode device 1820 illustrated in FIG. 18.

The communication device may minimize a degradation of radiation performance of the circuit 1910 corresponding to the first partial coil and the circuit 1920 corresponding to the second partial coil, and may also maximize a stacking efficiency using a 3D structure.

Figure 20:
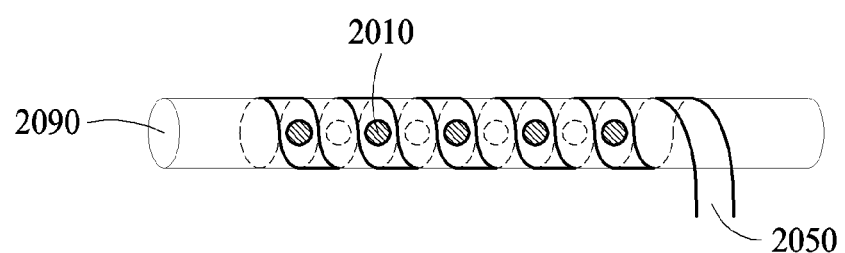
FIG. 20 is a diagram illustrating an example of an arrangement of electrodes of an electrode device.

FIG. 20 is a diagram illustrating an example of an arrangement of electrodes of an electrode device.

Referring to FIG. 20, an electrode device includes electrodes 2010.

The electrodes 2010 are arranged on a face of a substrate 2050 that is in contact with a target 2090 in a longitudinal direction of the substrate 2050. For example, the electrodes 2010 are arranged in line at preset or specified intervals therebetween along the substrate 2050. Each of the electrodes 2010 is allocated to one of a sensing channel and a stimulating channel. The electrodes 2010 are formed of a biocompatible metal.

The substrate 2050 is formed of a flexible material, and covers the target 2090. For example, the substrate 2050 is thin and long with a small width and a great length, and arranged to helically cover the target 2090. The substrate 2050 is provided in a form of a helical thread. The substrate 2050 is formed of a material suitable for a living body.

An electrode router (not shown) connects the electrodes 2010 and a processor. The electrode router is also referred to as an electrode router circuit as illustrated in FIGS. 13 and 14. The electrode router transfers, to the processor, an electrical signal detected or sensed through a first electrode among the electrodes 2010. The electrode router applies an electrical signal to a point of the target 2090 in contact with a second electrode that is different from the first electrode among the electrodes 2010. The first electrode is an electrode allocated to the sensing channel, and the second electrode is an electrode allocated to the stimulating channel.

Figure 21:
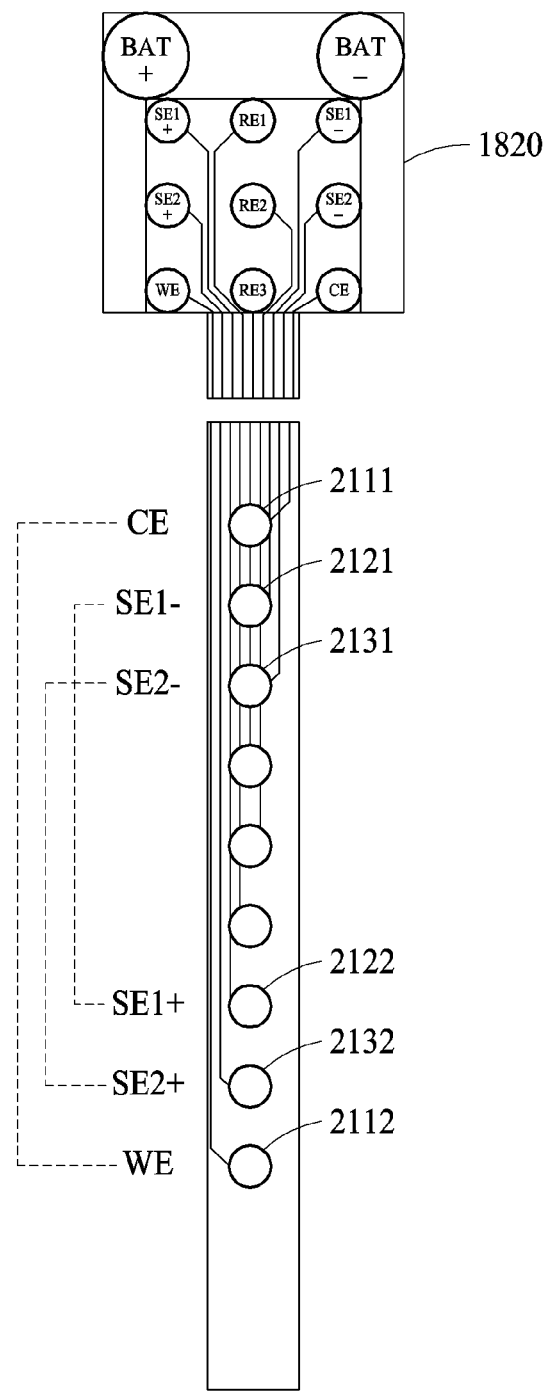
FIGS. 21 and 22 are diagrams illustrating examples of an arrangement of electrode channels of an electrode device.
Figure 22:
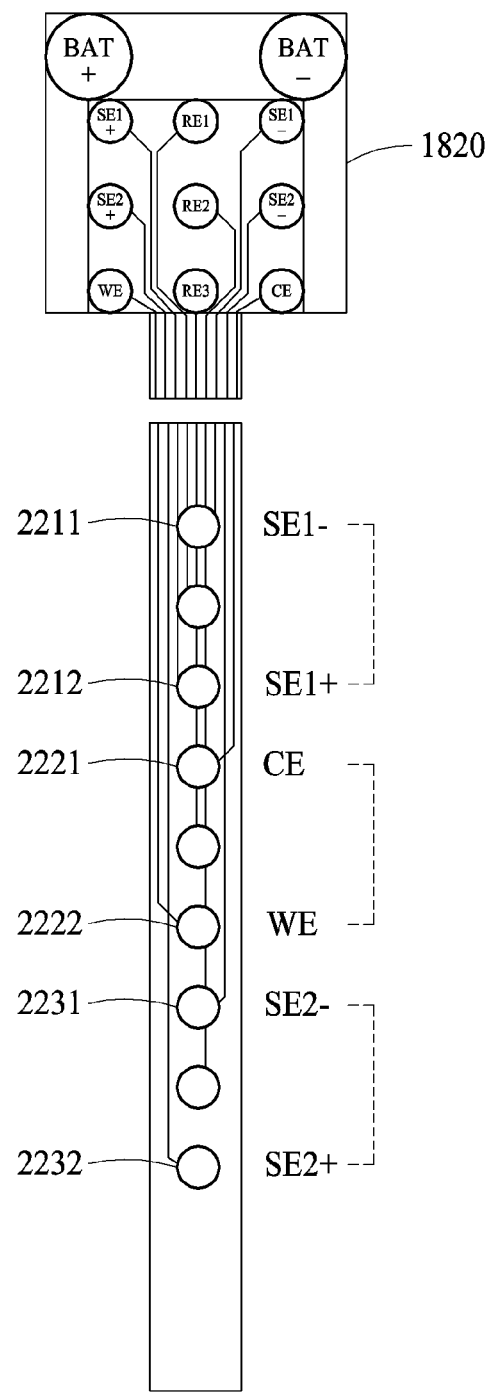

FIGS. 21 and 22 are diagrams illustrating examples of an arrangement of electrode channels of the electrode device 1820 of FIG. 18.

FIG. 21 is a diagram illustrating an example of an arrangement of electrodes on a substrate connected to the electrode device 1820 illustrated in FIG. 18.

In one example, electrodes are classified based on channels, and electrodes belonging to a same channel among the channels are arranged not to be adjacent to each other on a substrate. For example, a positive electrode and a negative electrode that correspond to a single differential signal in a same channel are arranged as far apart as possible on the substrate.

As illustrated in FIG. 21, a counter electrode CE 2111 and a working electrode WE 2112 of a stimulating channel are arranged as far apart as possible on the substrate. A negative electrode SE1− 2121 and a positive electrode SE1+ 2122 of a first sensing channel are arranged not to be adjacent to each other. Similarly, a negative electrode SE2− 2131 and a positive electrode SE2+ 2132 of a second sensing channel are arranged not to be adjacent to each other. A reference electrode RE of each channel is arranged on a central portion of the substrate, and operates as a ground.

Figure 25:
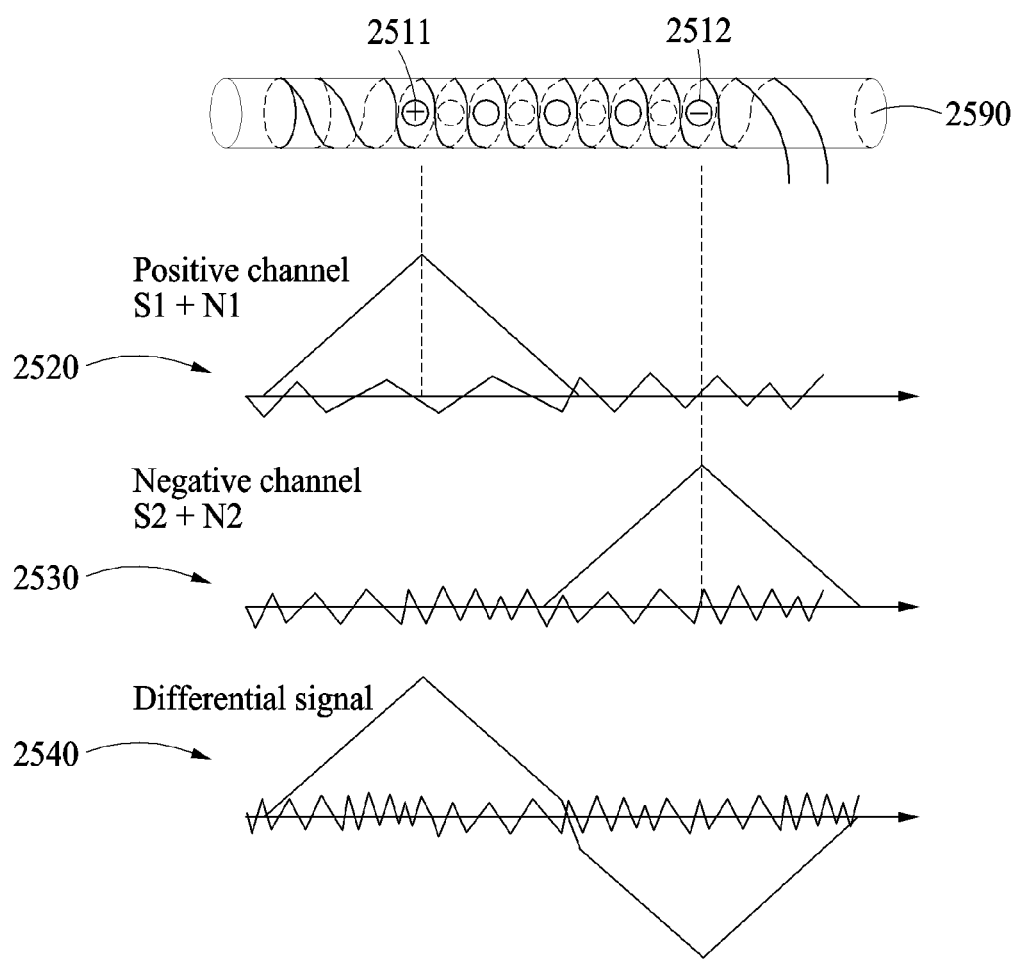

In a case in which corresponding electrodes in a same channel are arranged as far apart as possible from each other, a signal amplification effect may be obtained as illustrated in FIG. 25.

FIG. 22 is a diagram illustrating another example of an arrangement of electrodes on a substrate connected to the electrode device 1820 illustrated in FIG. 18.

In one example, electrodes are classified based on channels, and electrodes belonging to a same channel among the channels are arranged to be adjacent to each other on a substrate. For example, a positive electrode and a negative electrode that correspond to a single differential signal in a same channel are arranged to be adjacent to each other on the substrate.

As illustrated in FIG. 22, a negative electrode SE1− 2211 and a positive electrode SE1+ 2212 of a first sensing channel are arranged adjacent to each other along with a reference electrode RE. A negative electrode SE2− 2231 and a positive electrode SE2+ 2232 of a second sensing channel are arranged adjacent to each other along with a reference electrode RE. A counter electrode CE 2221 and a working electrode WE 2222 of a stimulating channel are arranged adjacent to each other along with a reference channel.

Figure 23:
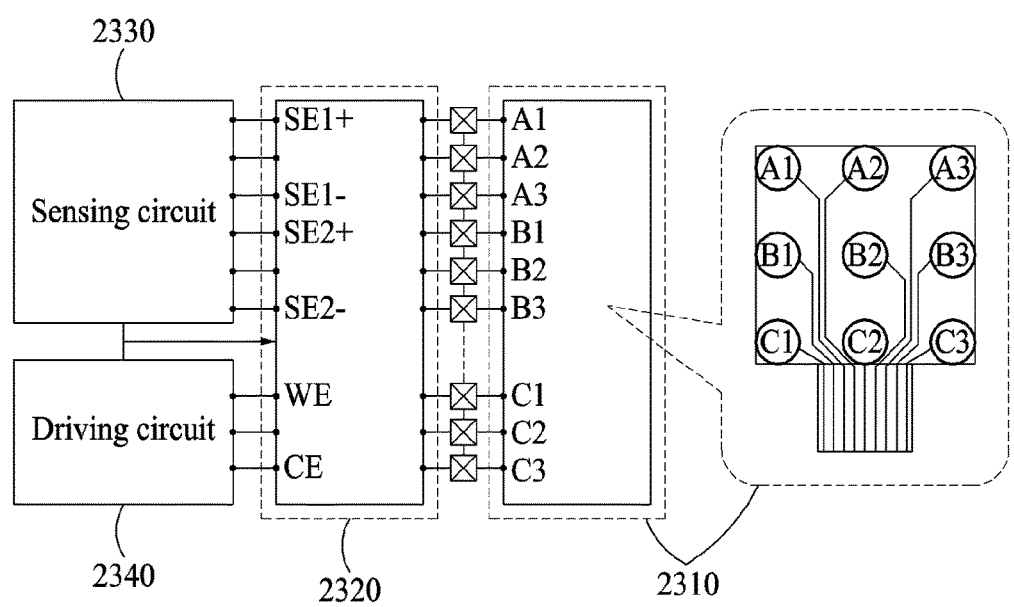
FIG. 23 is a diagram illustrating an example of a dynamic allocation of electrode channels of an electrode device.

FIG. 23 is a diagram illustrating an example of a dynamic allocation of electrode channels of an electrode device 2300.

Referring to FIG. 23, the electrode device 2300 includes an electrode interface 2310, an electrode router 2320, a sensing circuit 2330, and a driving circuit 2340.

The electrode interface 2310 includes electrodes and a substrate on which the electrodes are arranged.

The electrode router 2320 is connected to the electrodes on the substrate. The electrode router 2320 transfers an electrical signal received from each electrode to a processor (not shown) through the sensing circuit 2330 based on channels allocated to the electrodes. In addition, the electrode router 2320 transfers an electrical signal received from the processor to the electrode interface 2310 through the driving circuit 2340.

The sensing circuit 2330 detects or senses an electrical signal from a connected electrode through the electrode router 2320.

The driving circuit 2340 applies an electrical signal to a connected electrode through the electrode router 2320.

In one example, in response to a control command of the processor, the electrode router 2320 changes a mapping of a channel to be allocated to each electrode. Here, the term "allocate" may be used for both electrodes and channels, and allocating an electrode to a channel and allocating a channel to an electrode are construed herein as having a same meaning. For example, in response to the control command of the processor, the electrode router 2320 allocates a sensing channel of the electrode router 2320 to at least a portion (e.g., one or more) of the electrodes by connecting the at least a portion of the electrodes to the sensing circuit 2330. In addition, in response to the control command of the processor, the electrode router 2320 allocates a stimulating channel of the electrode router 2320 to at least a portion (e.g., one or more) of remaining electrodes among the electrodes by connecting the at least a portion of the remaining electrodes to the driving circuit 2340. As illustrated in FIG. 23, the electrodes include electrodes A1, A2, A3, B1, B2, B3, C1, C2, and C3, and the electrode router 2320 allocates, to the electrodes, a positive electrode SE1+ and a negative electrode SE− of a first sensing channel, a positive electrode SE2+ and a negative electrode SE2− of a second sensing channel, and a working electrode WE and a counter electrode CE of the stimulating channel.

As described above, the processor controls the electrode router 2320 to control a connection among the sensing circuit 2330, the driving circuit 2340, and the electrode interface 2310. For example, the processor allocates at least a portion of the electrodes to the sensing channel of the electrode router, and at least a portion of remaining electrodes among the electrodes to the stimulating channel of the electrode router 2320. For another example, the processor allocates at least a portion of the electrodes to the sensing channel of the electrode router 2320, and at least another portion of the electrodes to the stimulating channel of the electrode router 2320, based on an electrical signal detected from a target. Such a dynamic channel allocation performed based on the electrical signal detected from the target will be described in detail with reference to FIGS. 24 and 25.

Figure 24:
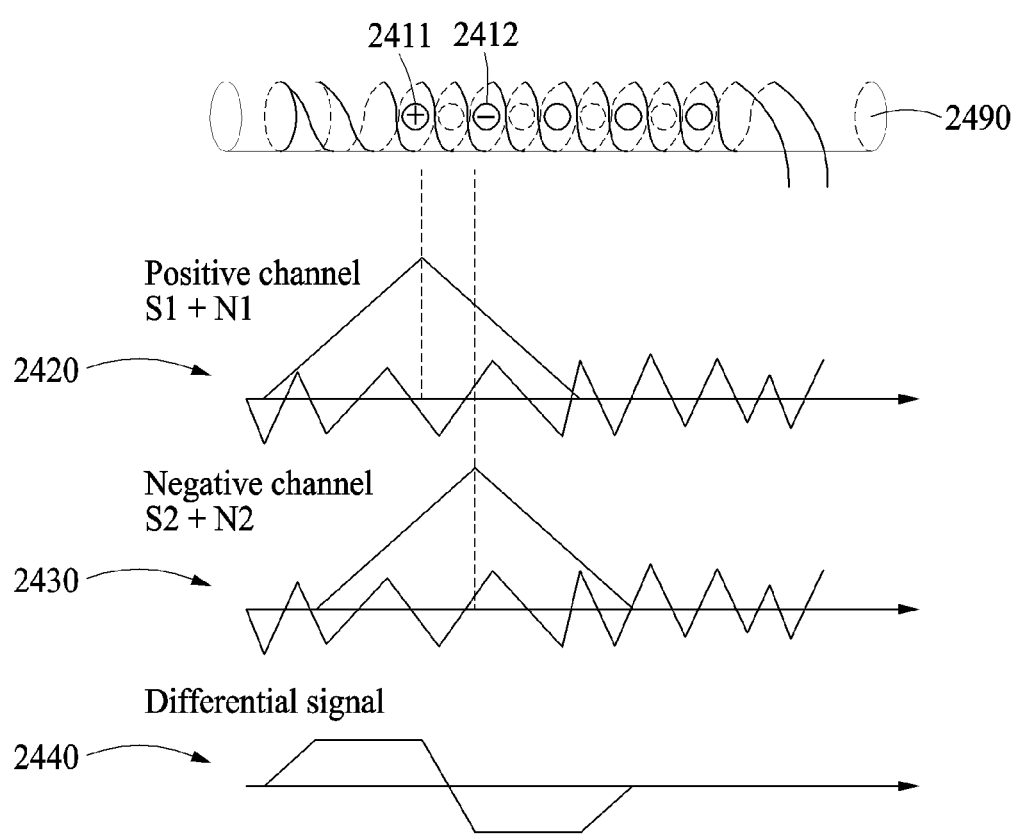
FIGS. 24 and 25 are diagrams illustrating examples of a differential signal based on an allocation of electrode channels.

FIGS. 24 and 25 are diagrams illustrating examples of a differential signal based on an allocation of electrode channels.

As described above, a processor may allocate a sensing channel to at least a portion of electrodes, and a stimulating channel to at least a portion of remaining electrodes among the electrodes.

For example, as illustrated in FIG. 24, in response to an electrical signal detected from a target 2490 including a threshold value or greater of common noise, the processor allocates the channels to the electrodes to arrange electrodes belonging to a same channel to be adjacent to each another on a substrate.

As illustrated in FIG. 24, in a case in which electrodes allocated to a same channel are arranged adjacent to each other, common noise is removed from a differential signal 2440 associated with a first signal 2420 detected from a positive channel 2411 of the sensing channel and a second signal 2430 detected from a negative channel 2412 of the sensing channel. Thus, the processor may obtain a signal that is robust against the common noise by arranging electrodes of a same channel to be adjacent to each other in response to the threshold value or greater of common noise being detected.

For another example, as illustrated in FIG. 25, in response to the electrical signal detected from a target 2590 including common noise of a value less than the threshold value, the processor allocates the channels to the electrodes to arrange electrodes belonging to a same channel not to be adjacent to each other on the substrate.

As illustrated in FIG. 25, in a case in which electrodes allocated to a same channel are arranged not to be adjacent to each other, an amplitude of a differential signal 2540 associated with a first signal 2520 detected from a positive channel 2511 of a sensing channel and a second signal 2530 detected from a negative channel 2512 of the sensing channel is amplified. Thus, in response to the common noise being low (e.g., less than the threshold value), the processor may obtain an amplified electrical signal by arranging electrodes of a same channel to be far apart from each other.

As described above, a processor of a wireless device, a communication device, and an electrode device may dynamically map channels to be allocated to linearly arranged electrodes based on a period and an amplitude of an electrical signal detected from a target being observed. Thus, after the wireless device is inserted in an object, the wireless device may determine an optimal electrode arrangement without being separated from the object.

In addition to detection, in terms of stimulation, the wireless device, the communication device, and the electrode device may apply an electrical signal to the target through a current path having a higher signal-to-noise ratio (SNR). Thus, power to be used for electrostimulation applied to the target may be adjusted, and thus power efficiency may be improved.

Figure 26:
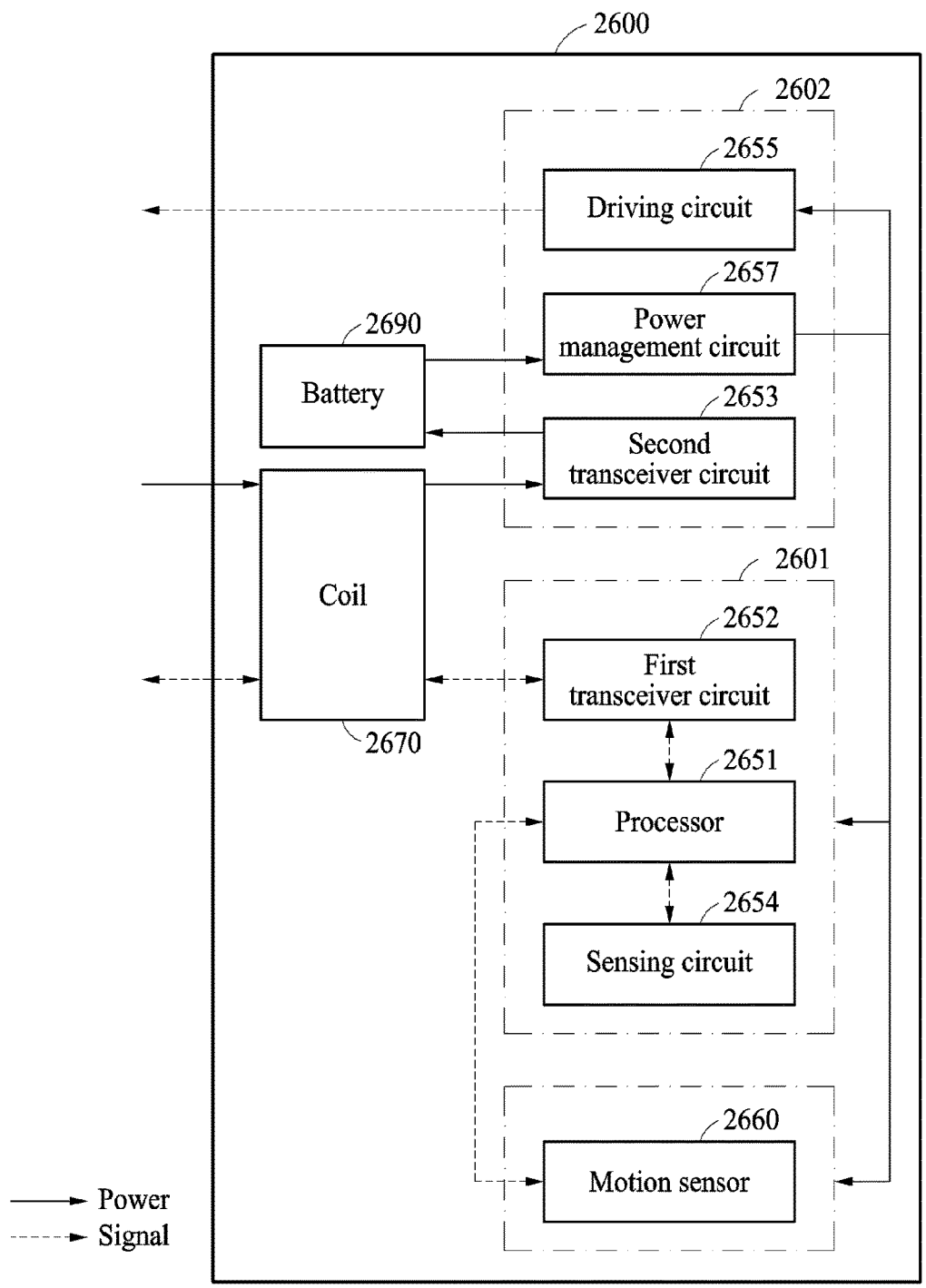
FIGS. 26 and 27 are diagrams illustrating another example of a configuration of a communication device.
Figure 27:
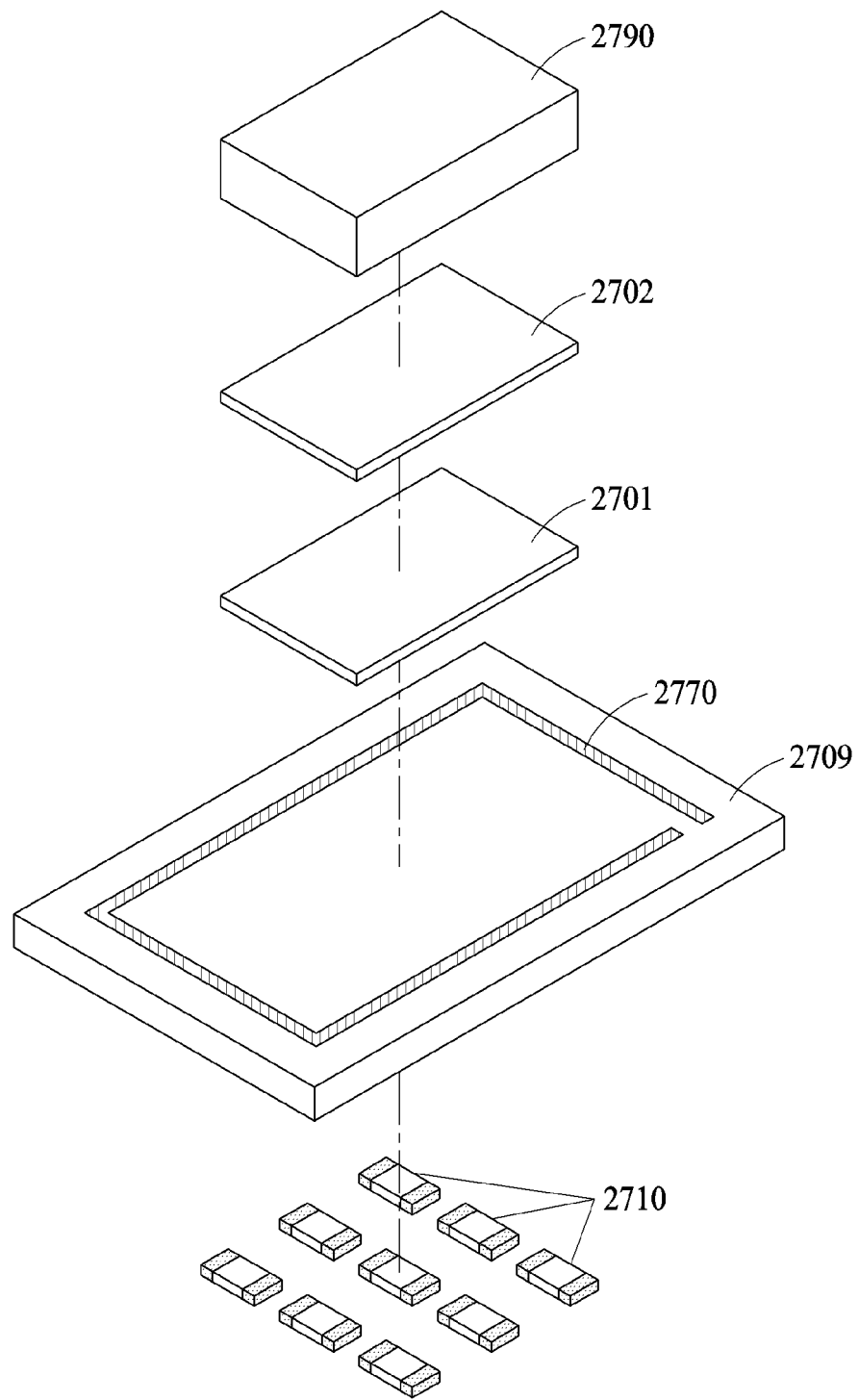

FIGS. 26 and 27 are diagrams illustrating another example of a configuration of a communication device 2600.

Referring to FIG. 26, the communication device 2600 includes a first chip package 2601, a second chip package 2602, a motion sensor 2660, a coil 2670, and a battery 2690. The first chip package 2601 and the second chip package 2602 may be embodied in a form of a single chip. However, the form is not limited to the example provided above, and thus the first chip package 2601 and the second chip package 2602 may be embodied in a form of separate chips.

The first chip package 2601 may be a chip configured to operate at a voltage less than or equal to a first threshold voltage. The voltage less than or equal to the first threshold voltage may also be referred to as a low voltage. In an example, a first transceiver circuit 2652, a processor 2651, and a sensing circuit 2654 that are included in the first chip package 2601 operate at such a low voltage. For example, when the first threshold voltage is designed to be 2 volts (V), the first chip package 2601 applies a low voltage of 1.8V to the first transceiver circuit 2652, the processor 2651, and the sensing circuit 2654.

However, examples are not limited to the example described above. For example, the first chip package 2601 may be configured to operate in a first voltage range. The first voltage range may be a range of the low voltage less than or equal to the first threshold voltage.

For example, when the first voltage range is designed to be 1.6V to 2V, the first chip package 2601 applies a low voltage of 1.7V or 1.9V to the first transceiver circuit 2652, the processor 2651, and the sensing circuit 2654. The first chip package 2601 operating at the low voltage may operate mainly to transmit a signal.

The second chip package 2602 may be a chip configured to operate at a voltage greater than or equal to a second threshold voltage. The voltage greater than or equal to the second threshold voltage may also be referred to as a high voltage. The second threshold voltage may be greater than the first threshold voltage. In an example, a second transceiver circuit 2653, a driving circuit 2655, and a power management circuit 2657 that are included in the second chip package 2602 operate at such a high voltage. For example, when the second threshold voltage is designed to be 11V, the second chip package 2602 applies a high voltage of 12V to the second transceiver circuit 2653, the driving circuit 2655, and the power management circuit 2657.

However, examples are not limited to the example described above. For example, the second chip package 2602 may be embodied to operate in a second voltage range. The second voltage range may be a range of the high voltage greater than or equal to the second threshold voltage. For example, when the second voltage range is designed to be 11V to 13V, the second chip package 2602 applies a high voltage of 11.5V or 12.5V to the second transceiver circuit 2653, the driving circuit 2655, and the power management circuit 2657. The second chip package 2602 operating at the high voltage may operate mainly to manage a voltage.

In FIG. 26, a solid line arrow indicates power transfer, and a broken line arrow indicates signal transfer. As illustrated, power received through the coil 2670 is transferred to the battery 2690 through the second transceiver circuit 2653. The power management circuit 2657 provides the power received from the battery 2690 to the remaining circuits. Also, a signal received through the coil 2670 is transferred to the processor 2651 through the first transceiver circuit 2652. The processor 2651 processes the signal and transfers the processed signal to other circuits, or processes a signal transferred from the other circuits.

In an example, the communication device 2600 reduces power consumption by applying, to the first chip package 2601, a voltage less than a voltage applied to the second chip package 2602.

The motion sensor 2660 senses a motion of the communication device 2600. The motion sensor 2660 is embodied as, for example, an acceleration sensor and a geomagnetic field sensor. The motion sensor 2660 may measure an acceleration applied to the communication device 2600.

The processor 2651, the first transceiver circuit 2652, and the second transceiver circuit 2653, the sensing circuit 2654, the driving circuit 2655, the power management circuit 2657, the coil 2670, and the battery 2690 may operate or be configured as described with reference to FIGS. 13 and 14.

FIG. 27 illustrates a stacked structure of a communication device 2700 corresponding to the communication device 2600 of FIG. 26.

Referring to FIG. 27, the communication device 2700 includes a structure in which a substrate 2709, a coil 2770, a first chip package 2701, a second chip package 2702, and a battery 2790 are stacked in a sequential order. For example, as illustrated, the components of the communication device 2700 are stacked on a first surface of the substrate 2709 in an order of the first chip package 2701, the second chip package 2702, and the battery 2790. In addition, a motion sensor may be stacked in a layer including the battery 2790, or stacked on the battery 2790.

A discrete element 2710 is stacked on a second surface of the substrate 2709 that is opposite to the first surface on which the first chip package 2701, the second chip package 2702, and the battery 2790 are staked. The discrete element 2710 is, for example, a decoupling capacitor.

The coil 2770, the first chip package 2701, the second chip package 2702, and the battery 2790 may operate or be configured as described with reference to the first chip package 2601, the second chip package 2602, and the battery 2690 of FIG. 26, and the substrate 2709 may be the same as the substrate 560 described above with reference to FIG. 5.

The processors 320, 1250, 1351, 1451, and 2651 in FIGS. 1, 12, 13, 14, and 26, respectively, and other components that perform the operations described in this application are implemented by hardware components configured to perform the operations described in this application that are performed by the hardware components. Examples of hardware components that may be used to perform the operations described in this application where appropriate include controllers, sensors, generators, drivers, memories, comparators, arithmetic logic units, adders, subtractors, multipliers, dividers, integrators, and any other electronic components configured to perform the operations described in this application. In other examples, one or more of the hardware components that perform the operations described in this application are implemented by computing hardware, for example, by one or more processors or computers. A processor or computer may be implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices that is configured to respond to and execute instructions in a defined manner to achieve a desired result. In one example, a processor or computer includes, or is connected to, one or more memories storing instructions or software that are executed by the processor or computer. Hardware components implemented by a processor or computer may execute instructions or software, such as an operating system (OS) and one or more software applications that run on the OS, to perform the operations described in this application. The hardware components may also access, manipulate, process, create, and store data in response to execution of the instructions or software. For simplicity, the singular term "processor" or "computer" may be used in the description of the examples described in this application, but in other examples multiple processors or computers may be used, or a processor or computer may include multiple processing elements, or multiple types of processing elements, or both. For example, a single hardware component or two or more hardware components may be implemented by a single processor, or two or more processors, or a processor and a controller. One or more hardware components may be implemented by one or more processors, or a processor and a controller, and one or more other hardware components may be implemented by one or more other processors, or another processor and another controller. One or more processors, or a processor and a controller, may implement a single hardware component, or two or more hardware components. A hardware component may have any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

Instructions or software to control computing hardware, for example, one or more processors or computers, to implement the hardware components and perform the methods as described above may be written as computer programs, code segments, instructions or any combination thereof, for individually or collectively instructing or configuring the one or more processors or computers to operate as a machine or special-purpose computer to perform the operations that are performed by the hardware components and the methods as described above. In one example, the instructions or software include machine code that is directly executed by the one or more processors or computers, such as machine code produced by a compiler. In another example, the instructions or software includes higher-level code that is executed by the one or more processors or computer using an interpreter. The instructions or software may be written using any programming language based on the block diagrams and the flow charts illustrated in the drawings and the corresponding descriptions in the specification, which disclose algorithms for performing the operations that are performed by the hardware components and the methods as described above.

The instructions or software to control computing hardware, for example, one or more processors or computers, to implement the hardware components and perform the methods as described above, and any associated data, data files, and data structures, may be recorded, stored, or fixed in or on one or more non-transitory computer-readable storage media. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, and any other device that is configured to store the instructions or software and any associated data, data files, and data structures in a non-transitory manner and provide the instructions or software and any associated data, data files, and data structures to one or more processors or computers so that the one or more processors or computers can execute the instructions. In one example, the instructions or software and any associated data, data files, and data structures are distributed over network-coupled computer systems so that the instructions and software and any associated data, data files, and data structures are stored, accessed, and executed in a distributed fashion by the one or more processors or computers.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A communication device, comprising:
a coil disposed around a core area of the communication device;
a processor disposed only in the core area and configured to establish communication with an external device through the coil; and
a discrete element disposed on the coil and connected to the processor through a via, wherein the discrete element comprises any one or any combination of any two or more of a capacitor, an inductor, and a resistor.

2. The communication device of claim 1, wherein the processor is disposed in a layer distinguished from the coil.

3. The communication device of claim 1, wherein the discrete element comprises a passive electronic component configured to separate voltages, by electrically decoupling circuits of circuits in a chip including the processor.

4. The communication device of claim 1, wherein the discrete element is connected to a chip comprising the processor through the via, and is arranged in an outer edge ring area of the coil in a layer distinguished from the coil.

5. The communication device of claim 1, further comprising:
a first transceiver circuit configured to transmit and receive, through the coil, a signal of a first bandwidth; and
a second transceiver circuit configured to transmit and receive, through the coil, a signal of a second bandwidth that is different from the first bandwidth,
wherein the first transceiver circuit and the second transceiver circuit are included in a chip comprising the processor.

6. The communication device of claim 5, wherein
the first transceiver circuit is configured to operate at a voltage less than or equal to a first threshold voltage, and
the second transceiver circuit is configured to operate at a voltage greater than or equal to a second threshold voltage that is greater than the first threshold voltage.

7. The communication device of claim 1, further comprising:
an electrode router circuit connected to electrodes of an electrode device,
wherein the electrode router circuit is included in a chip comprising the processor.

8. The communication device of claim 7, wherein
the electrode router circuit is configured to connect a first electrode among the electrodes to a sensing circuit, and connect a second electrode among the electrodes to a driving circuit,
the sensing circuit is configured to detect, through the first electrode, an electrical signal corresponding to a point to which the first electrode is attached, and
the driving circuit is configured to apply, through the second electrode, an electrical signal to a point to which the second electrode is attached.

9. The communication device of claim 8, wherein
the sensing circuit is configured to operate at a voltage less than or equal to a first threshold voltage, and
the driving circuit is configured to operate at a voltage greater than or equal to a second threshold voltage that is greater than the first threshold voltage.

10. The communication device of claim 1, wherein the coil comprises
a first partial coil configured to resonate in a first bandwidth, and
a second partial coil configured to resonate in a second bandwidth that is different from the first bandwidth, and
the first partial coil and the second partial coil share a loop.

11. The communication device of claim 10, wherein
the first partial coil comprises a loop configured to generate a magnetic field in a first direction, and
the second partial coil comprises a loop configured to generate an electric field in the first direction.

12. The communication device of claim 1, further comprising:
an embedded element disposed in a layer distinguished from a layer comprising the coil and a layer including the processor, and connected to the processor through the via, wherein the embedded element comprises either one or both of a capacitor or an inductor; and
a motion sensor configured to sense a motion of the communication device.

13. The communication device of claim 1, wherein a chip comprising the processor is spaced from the coil by a distance greater than or equal to a threshold distance.

14. The communication device of claim 1, wherein the processor is connected to electrodes of an electrode device arranged to cover a target area associated with an object, and is configured to receive an electrical signal from or provide an electrical signal to some of the electrodes.

15. The communication device of claim 14, wherein the processor is configured to allocate a sensing channel configured to receive the electrical signal from the electrodes using one or more electrodes among the electrodes, and allocate a stimulating channel configured to provide an electrical signal to the target area using one or more remaining electrodes among the electrodes, based on the received electrical signal.

16. A communication device, comprising:
a coil disposed around a core area of the communication device;
a processor disposed in the core area and configured to establish communication with an external device through the coil;
a discrete element disposed on the coil and connected to the processor through a via, wherein the discrete element comprises any one or any combination of any two or more of a capacitor, an inductor, and a resistor, which is connected to a chip comprising the processor through the via; and
an electrode router circuit connected to electrodes of an electrode device, wherein
the electrode router circuit is configured to connect a first electrode among the electrodes to a sensing circuit, and connect a second electrode among the electrodes to a driving circuit,
the sensing circuit is configured to detect, through the first electrode, an electrical signal corresponding to a point to which the first electrode is attached, and
the driving circuit is configured to apply, through the second electrode, an electrical signal to a point to which the second electrode is attached.

17. The communication device of claim 16, wherein the electrode router circuit is included in a chip comprising the processor.

18. A communication device, comprising:
a coil disposed around a core area of the communication device;
a processor disposed in the core area and configured to establish communication with an external device through the coil,
wherein the processor is connected to electrodes arranged to cover a target area associated with an object, and is configured to receive an electrical signal from or provide an electrical signal to some of the electrodes, and
wherein the processor is configured to allocate a sensing channel configured to receive the electrical signal from the electrodes using one or more electrodes among the electrodes, and allocate a stimulating channel configured to provide an electrical signal to the target area using one or more remaining electrodes among the electrodes, based on the received electrical signal; and
a discrete element disposed on the coil and connected to the processor through a via, wherein the discrete element comprises any one or any combination of any two or more of a capacitor, an inductor, and a resistor, which is connected to a chip comprising the processor through the via.

\* \* \* \* \*